United States Patent
Elmaleh et al.

(10) Patent No.: US 10,561,612 B2
(45) Date of Patent: Feb. 18, 2020

(54) POWDERED FORMULATIONS OF CROMOLYN SODIUM AND IBUPROFEN

(71) Applicants: AZTherapies, Inc., Boston, MA (US); The General Hospital Corporation, Boston, MA (US)

(72) Inventors: David R. Elmaleh, Newton, MA (US); Juan B. Gonzalez, Rochester, NH (US)

(73) Assignees: The General Hospital Corporation, Boston, MA (US); AZTherapies, Inc., Boston, MA (US)

( * ) Notice: Subject to any disclaimer, the term of this patent is extended or adjusted under 35 U.S.C. 154(b) by 0 days.

(21) Appl. No.: 15/838,753

(22) Filed: Dec. 12, 2017

(65) Prior Publication Data

US 2019/0022006 A1    Jan. 24, 2019

Related U.S. Application Data

(60) Provisional application No. 62/534,848, filed on Jul. 20, 2017.

(51) Int. Cl.
| | |
|---|---|
| *A61K 9/14* | (2006.01) |
| *A61K 9/00* | (2006.01) |
| *A61K 9/16* | (2006.01) |
| *A61P 25/28* | (2006.01) |
| *A61K 31/352* | (2006.01) |
| *A61K 31/192* | (2006.01) |

(52) U.S. Cl.
CPC ............. *A61K 9/14* (2013.01); *A61K 9/0075* (2013.01); *A61K 31/192* (2013.01); *A61K 31/352* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 3,419,578 A | 12/1968 | Fitzmaurice et al. |
| 3,634,582 A | 1/1972 | Hartley et al. |
| 3,686,412 A | 8/1972 | Fitzmaurice et al. |
| 3,957,965 A | 5/1976 | Hartley et al. |
| 4,120,285 A | 10/1978 | Nugent |
| 4,405,735 A | 9/1983 | Wiezer et al. |
| 4,429,545 A | 2/1984 | Steinberg |
| 4,481,206 A | 11/1984 | Spiegel et al. |

(Continued)

FOREIGN PATENT DOCUMENTS

| | | |
|---|---|---|
| CA | 2408793 A1 | 12/2001 |
| CN | 101754746 A | 6/2010 |

(Continued)

OTHER PUBLICATIONS

International Search Report of PCT Application No. PCT/US2017/65727, dated Feb. 12, 2018.

(Continued)

*Primary Examiner* — Kyung S Chang
(74) *Attorney, Agent, or Firm* — Foley Hoag LLP

(57) ABSTRACT

The invention is directed to a composition comprising cromolyn sodium and ibuprofen, wherein the cromolyn sodium is micronized and the cromolyn sodium and ibuprofen are present in a weight ratio of 1:1-2. In one embodiment, the ibuprofen is passed through a sieve, such as a 300 μm sieve and to methods of making the same.

12 Claims, 17 Drawing Sheets

(56) References Cited

U.S. PATENT DOCUMENTS

| | | |
|---|---|---|
| 4,996,296 A | 2/1991 | Pecht et al. |
| 5,567,720 A | 10/1996 | Averback |
| 5,594,142 A | 1/1997 | Gaa et al. |
| 5,655,523 A | 8/1997 | Hodson et al. |
| 5,830,920 A | 11/1998 | Chucholowski et al. |
| 5,904,937 A | 5/1999 | Augello et al. |
| 6,168,776 B1 | 1/2001 | Klunk et al. |
| 6,197,963 B1 | 3/2001 | Hirschmann et al. |
| 6,309,623 B1 | 10/2001 | Weers et al. |
| 6,696,039 B2 | 2/2004 | Kung et al. |
| 6,911,466 B2 | 6/2005 | Koo et al. |
| 6,946,116 B2 | 9/2005 | Kung et al. |
| 6,972,127 B2 | 12/2005 | Schenk |
| 7,160,559 B1 | 1/2007 | McGee et al. |
| 7,858,803 B2 | 12/2010 | Elmaleh et al. |
| 8,381,454 B1 | 2/2013 | Robinson |
| 8,613,920 B2 | 12/2013 | Lieberburg et al. |
| 8,617,517 B2 | 12/2013 | Elmaleh et al. |
| 8,765,742 B2 | 7/2014 | Hilfiker et al. |
| 9,283,230 B2 | 3/2016 | Clunas et al. |
| 9,855,276 B2 | 1/2018 | Elmaleh |
| 9,861,608 B2 | 1/2018 | Elmaleh et al. |
| 9,913,847 B2 | 3/2018 | Elmaleh |
| 9,918,992 B2 | 3/2018 | Elmaleh |
| 9,925,282 B2 | 3/2018 | Elmaleh et al. |
| 9,968,618 B1 | 5/2018 | Elmaleh |
| 10,058,530 B2 | 8/2018 | Elmaleh |
| 10,188,757 B2 | 1/2019 | Elmaleh |
| 10,245,331 B2 | 4/2019 | Elmaleh |
| 10,251,961 B2 | 4/2019 | Elmaleh |
| 2002/0009491 A1 | 1/2002 | Rothbard et al. |
| 2002/0016359 A1 | 2/2002 | Hellberg et al. |
| 2002/0091100 A1 | 7/2002 | Lezdey et al. |
| 2002/0107173 A1 | 8/2002 | Friedhoff et al. |
| 2004/0176469 A1 | 9/2004 | Thomas |
| 2004/0223918 A1 | 11/2004 | Pham et al. |
| 2004/0259952 A1 | 12/2004 | Abbas et al. |
| 2006/0051319 A1 | 3/2006 | Yoo |
| 2006/0159629 A1 | 7/2006 | Tarara et al. |
| 2006/0240007 A1 | 10/2006 | Sanders |
| 2006/0276455 A1 | 12/2006 | Lindsberg et al. |
| 2007/0015813 A1 | 1/2007 | Carter et al. |
| 2007/0086981 A1 | 4/2007 | Meijer et al. |
| 2007/0093457 A1 | 4/2007 | Arber et al. |
| 2007/0107173 A1 | 5/2007 | Yamada |
| 2007/0178166 A1 | 8/2007 | Bernstein et al. |
| 2007/0193577 A1 | 8/2007 | Keller |
| 2007/0249644 A1 | 10/2007 | Pearson et al. |
| 2007/0293538 A1 | 12/2007 | Hobden |
| 2008/0021085 A1 | 1/2008 | Koo et al. |
| 2009/0110679 A1 | 4/2009 | Li et al. |
| 2009/0155256 A1 | 6/2009 | Black et al. |
| 2010/0113613 A1 | 5/2010 | McLaurin et al. |
| 2010/0143251 A1 | 6/2010 | Tamagnan et al. |
| 2010/0173960 A1 | 7/2010 | Cruz et al. |
| 2010/0234295 A1 | 9/2010 | Chen |
| 2010/0236550 A1 | 9/2010 | Zeng et al. |
| 2010/0266531 A1 | 10/2010 | Hsieh et al. |
| 2010/0298389 A1 | 11/2010 | Elmaleh et al. |
| 2011/0060138 A1 | 3/2011 | Elmaleh et al. |
| 2011/0129530 A1* | 6/2011 | Venkatesh ............ A61K 9/0056 424/470 |
| 2011/0132434 A1 | 6/2011 | Correia et al. |
| 2011/0262442 A1 | 10/2011 | Hamilton et al. |
| 2012/0058049 A1 | 3/2012 | Elmaleh et al. |
| 2012/0082727 A1 | 4/2012 | Cocconi et al. |
| 2012/0118991 A1 | 5/2012 | Keller et al. |
| 2012/0121656 A1 | 5/2012 | Watson et al. |
| 2012/0134929 A1 | 5/2012 | McGrath et al. |
| 2012/0165366 A1 | 6/2012 | Ibrahim et al. |
| 2012/0175082 A1 | 7/2012 | Kmetovicz et al. |
| 2014/0140927 A1 | 5/2014 | Elmaleh et al. |
| 2014/0228304 A1 | 8/2014 | Jones et al. |
| 2015/0224077 A1 | 8/2015 | Gerhart et al. |
| 2015/0224078 A1 | 8/2015 | Gerhart et al. |
| 2015/0283113 A1 | 10/2015 | Elmaleh |
| 2016/0158150 A1 | 6/2016 | Morton et al. |
| 2016/0310503 A1 | 10/2016 | Elmaleh |
| 2017/0290797 A1 | 10/2017 | Elmaleh |
| 2018/0169277 A1 | 6/2018 | Elmaleh |
| 2018/0177789 A1 | 6/2018 | Elmaleh |
| 2018/0177790 A1 | 6/2018 | Elmaleh |
| 2018/0177791 A1 | 6/2018 | Elmaleh |
| 2018/0193491 A1 | 7/2018 | Elmaleh |
| 2018/0193492 A1 | 7/2018 | Elmaleh |
| 2018/0344682 A1 | 12/2018 | Elmaleh |

FOREIGN PATENT DOCUMENTS

| | | |
|---|---|---|
| CN | 101848733 A | 9/2010 |
| EP | 1632242 A2 | 3/2006 |
| EP | 2322163 A1 | 5/2011 |
| EP | 2377860 A1 | 10/2011 |
| GB | 1144906 A | 3/1969 |
| GB | 1257162 A | 12/1971 |
| JP | S56-043448 B1 | 10/1981 |
| JP | 2001151673 A | 6/2001 |
| JP | 2005510535 A | 4/2005 |
| JP | 2007-534693 A | 11/2007 |
| JP | 2009-536918 A | 10/2009 |
| JP | 2010-510254 A | 4/2010 |
| JP | 2012-515712 A | 7/2012 |
| JP | 2012516356 A | 7/2012 |
| WO | WO-90/09789 A2 | 9/1990 |
| WO | WO-98/34596 A2 | 8/1998 |
| WO | WO-99/16422 A1 | 4/1999 |
| WO | WO-02/28820 A1 | 4/2002 |
| WO | WO-03/045331 A2 | 6/2003 |
| WO | WO-2005/104712 A2 | 11/2005 |
| WO | WO-2007/094718 A1 | 8/2007 |
| WO | WO-2008/013799 A2 | 1/2008 |
| WO | WO-2008/061373 A1 | 5/2008 |
| WO | WO-2008/128981 A1 | 10/2008 |
| WO | WO-2008/131298 A2 | 10/2008 |
| WO | WO-2009/010770 A2 | 1/2009 |
| WO | WO-2009/133128 A1 | 11/2009 |
| WO | WO-2010/088455 A2 | 8/2010 |
| WO | WO-2011/136754 A1 | 11/2011 |
| WO | WO-2014/066318 A1 | 5/2014 |
| WO | WO-2015/002703 A1 | 1/2015 |
| WO | WO-2015061397 A1 | 4/2015 |
| WO | WO 2016/196401 A1 | 12/2016 |
| WO | WO-2017091644 A1 | 6/2017 |
| WO | WO-2018/045217 A1 | 3/2018 |

OTHER PUBLICATIONS

Aisen et al., "Effects of rofecoxib or naproxen vs placebo on Alzheimer disease progression: a randomized controlled trial," JAMA, 289(21):2819-2826 (2003).

Akiyama et al., "Inflammation and Alzheimer's Disease," Neurobiol Aging, 21(3): 383-421 (2000).

Alafuzoff et al., "Lower counts of astroglia and activated microglia in patients with Alzheimer's disease with regular use of non-steroidal anti-inflammatory drugs," J Alzheimers Dis, 2(1):37-46 (2000).

Albert et al., "Effects of age on the clinical pharmacokinetics of ibuprofen," Am J Med, 77(1, Part 1):47-50 (1984).

Albert et al., "Pharmacokinetics of ibuprofen," Am J Med, 77(1A):40-46 (1984).

Aswania et al., "Relative bioavailability of sodium cromoglycate to the lung following inhalation, using urinary excretion," J Clin Pharmacol, 47:613-618 (1999).

Bannworth et al., "Stereoselective disposition of ibuprofen enantiomers in human cerebrospinal fluid.," Br J Clin Pharmacol, 40(3):266-269 (1995).

Basek et al., "Efficacy of an Isotonic Small Droplet Size Nebulized DSCG on Asthma Control in Children," Acta Paediatrica, 99(Suppl 462):115 (2010).

Beach et al., "Cromolyn sodium toxicity studies in primates," Toxicol Appl Pharmacol, 57(3):367-400 (1981).

(56) References Cited

OTHER PUBLICATIONS

Berg et al., "Pharmaceutical salts," J Pharm Sci, 66(1):1-19 (1977).
Bodor et al., "Improved delivery through biological membranes VII. Dermal delivery of cromoglycic acid (cromolyn) via its prodrugs," International Journal of Pharmaceutics, 7(1):63-75 (1980).
Bot et al., "Perivascular mast cells promote atherogenesis and induce plaque destabilization in apolipoprotein E-deficient mice," Circulation, 115(19):2516-2525 (2007).
Breitner et al., "Extended results of the Alzheimer's disease anti-inflammatory prevention trial," Alzheimers Dement, 7(4):402-411 (2011).
Breitner, "Alzheimer disease: The changing view," Annals Neurol, 49(3):418-419 (2001).
Broe et al., "Anti-inflammatory drugs protect against Alzheimer disease at low doses," Arch Neurol, 57:1586-1591 (2000).
Bulic et al., "Tau protein and tau aggregation inhibitors," Neuropharmacology, 59: 276-289 (2010).
Byron et al., "Selection and Validation of Cascade Impactor Test Methods," Respiratory Drug Delivery IX, 1: 169-178 (2004).
Cacabelos, R., "Donepezil in Alzheimer's disease: From conventional trials to pharmacogenetics," Neuropsychiatric Disease and Treatment 2007:3(3), pp. 303-333.
Cairns, et al., "Synthesis and Structure-Activity Relationships of Disodium Cromoglycate and Some Related Compounds, Journal of Medicinal Chemistry," 1972, 15(6):583-589.
Chen et al., "Current experimental therapy for Alzheimer's Disease," Curr Neuropharmacol, 5(2): 127-134 (2007).
Cole et al., "Mechanisms of action of non-steroidal anti-inflammatory drugs for the prevention of Alzheimer's disease," CNS Neurol Disord Drug Targets, 9(2):140-148 (2010).
Cummings, "Alzheimer's Disease," N Engl J Med, 351(1):56-67 (2004).
Davies, "Clinical pharmacokinetics of ibuprofen. The first 30 years," Clin Pharmacokinet, 34(2):101-154 (1998).
Deiana, S. et al., "Methylthioninium Chloride Versus Rivastigmine and Their Co-Administration Efficacy in Reversing Scopolamine-Induced Cognitive Deficits in a Pharmacological Mouse Model of Alzheimer's Disease," Alzheimer's & Dementia, 4(4):T499 (2008).
Doody et al., "Donepezil treatment of patients with MCI: a 48-week randomized, placebo-controlled trial," Neurology, 72(18):1555-1581 (2009).
Etminan et al., "Effect of non-steroidal anti-inflammatory drugs on risk of Alzheimer's disease: systematic review and meta-analysis of observational studies," Brit Med J, 327:128-131 (2003).
European Search Report for EP Application No. 13848340 dated Feb. 11, 2016.
European Search Report for European Application No. 14819448.3 dated Feb. 9, 2017.
Extended European Search Report, EP 10736439.0 dated Jun. 19, 2012.
Extended European Search Report, EP 14855211.0, dated May 29, 2017.
Findeis et al., "Design and testing of inhibitors of fibril formation," Methods Enzymol, 309:476-488 (1999).
Findeis et al., "Modified-peptide inhibitors of amyloid β-peptide polymerization," Biochemistry, 38(21):6791-6800 (1999).
Galimberti et al., "Disease-modifying treatments for Alzheimer's disease," Ther Adv Neurol Disord, 4(4): 203-216 (2011).
Garmise, "Novel Dry Powder Preparations of Whole Inactivated Influenza Virus for Nasal Vaccination," Dissertation, University of North Carolina at Chapel Hill (2007).
Gasparini et al., "Non-steroidal anti-inflammatory drugs (NSAIDs) in Alzheimer's disease: old and new mechanisms of action," J Neurochem, 91(3):521-536 (2004).
Gilani et al., "Influence of Formulation Variables and Inhalation Device on the Deposition Profiles of Cromolyn Sodium Dry Powder Aerosols," DARU vol. 12, No. 3, p. 123-130, 2004.
Griffin, "What causes Alzheimer's?" The Scientist, 25:36-40 (2011).
Guchardi, R. et al., "Influence of fine lactose and magnesium stearate on low dose dry powder inhaler formulations," International Journal of Pharmaceutics 348 (2008) 10-17.
Guo et al., "Comparison of Delivery Characteristics from a Combination Metered-Dose Inhaler Using the Andersen Cascade Impactor and the Next Generation Pharmaceutical Impactor," J Pharm Sci, 97(8): 3321-3334 (2008).
Gwin et al., "Cromolyn sodium in the treatment of asthma associated with aspirin hypersensitivity and nasal polyps," Chest, 72(2):148-153 (1977).
Haass et al., "Soluble protein oligomers in neurodegeneration: lessons from the Alzheimer's amyloid [beta]-peptide," Nat Rev Mal Cell Biol, 8(2):101-112 (2007).
Hashimoto et al., "Apolipoprotein E, especially apolipoprotein E4, increases the oligomerization of amyloid β peptide," J Neurosci, 32(43):15181-15192 (2012).
He Xiaoliang et al., "Progress of Inhaled Devices for Asthma," Journal of Applied Clinical Pediatrics, 22(4):309-311 (2007).
Heneka et al., "Acute treatment with the PPARγ agonist pioglitazone and ibuprofen reduces glial inflammation and Aβ1-42 levels in APPV717I transgenic mice," Brain, 128:1442-1453 (2005).
Hoozemans et al., "Soothing the inflamed brain: effect of non-steroidal anti-inflammatory drugs on Alzheimer's disease pathology," CNS Neurol Disord Drug Targets, 10(1):57-67 (2011).
Hori et al., "A Food and Drug Administration-approved asthma therapeutic agent impacts amyloid β in the brain in a transgenic model of Alzheimer disease," J Biol Chem, 290(4):1966-1978 (2015).
Huang et al., "Acute stress induces cardiac mast cell activation and histamine release, effects that are increased in Apolipoprotein E knockout mice.," Cardiovasc Res, 55(1):150-160 (2002).
Huang et al., "Stress-induced interleukin-6 release in mice is mast cell-dependent and more pronounced in Apolipoprotein E knockout mice," Cardiovasc Res, 59(1):241-249 (2003).
Imbimbo et al., "Are NSAIDs useful to treat Alzheimer's disease or mild cognitive impairment?," Front Aging Neurosci, 2(Article 19):pp. 1-14 (2010).
Imbimbo, "An update on the efficacy of non-steroidal anti-inflammatory drugs in Alzheimer's disease," Expert Opinion on Investigational Drugs, 2009; 18(8), pp. 1147-1168.
Intal Approval Package, Center for Drug Evaluation and Research, application 75-175, pp. 1-5 (Dec. 12, 1997).
International Search Report and Written Opinion for International Application No. PCT/US2013/066069 dated Mar. 13, 2014.
International Search Report and Written Opinion for International Application No. PCT/US16/63143 dated Feb. 6, 2017.
International Search Report and Written Opinion for International Application No. PCT/US16/63462 dated Feb. 1, 2017.
International Search Report and Written Opinion for International Application No. PCT/US2010/022495 dated Nov. 10, 2010.
International Search Report and Written Opinion for International Application No. PCT/US2014/061694 dated Jan. 2, 2015.
International Search Report and Written Opinion for International Application No. PCT/US2017/049702 dated Dec. 26, 2017.
International Search Report for International Application No. PCT/US14/39118 dated Sep. 18, 2014.
Jin et al., "Mast cells are early responders after hypoxia-ischemia in immature rat brain," Stroke, 40(9):3107-3112 (2009).
Karran et al., "The amyloid cascade hypothesis for Alzheimer's disease: an appraisal for the development of therapeutics," Nat Rev, 10(9):698-712 (2011).
Keller et al., "Have inadequate delivery systems hampered the clinical success of inhaled disodium cromoglycate? Time for reconsideration," Exp Opin Drug Deliv, 8(1):1-17 (2011).
Kelley et al., "The molecular role of mast cells in atherosclerotic cardiovascular disease," Mol Med Today, 6:304-308 (2000).
Knowles et al., "Donepezil in Alzheimer's disease: an evidence-based review of its impact on clinical and economic outcomes," Core Evid, 1(3):195-219 (2006).
Kohman et al., "Neurogenesis, inflammation and behavior," Brain Behav Immun, 27C:22-32 (2013).
Koo et al., "Amyloid diseases: Abnormal protein aggregation in neurodegeneration, " PNAS, 96:9989-9990 (1999).

(56) References Cited

OTHER PUBLICATIONS

Kotilinek et al., "Cyclooxygenase-2 inhibition improves amyloid-β-mediated suppression of memory and synaptic plasticity," Brain, 131(3):651-664 (2008).
Krstic et al., "Deciphering the mechanism underlying late-onset Alzheimer disease," Nat Rev Neurol, 9:25-34(2013).
Kwong et al., "Comparison of Nebulized Particle Size Distribution with Malvern Laser Diffraction Analyzer Versus Andersen Cascade Impactor and Low-Flow Marple Personal Cascade Impactor," J Aerosol Med, 13(4): 303-314 (2000).
Lanz et al., "The γ-Secretase Inhibitor N-[N-(3,5-Difluorophenacetyl)-L-alanyl]-S- phenylglycine t-butyl Ester Reduces Aβ Levels in Vivo in Plasma and Cerebrospinal Fluid in Young (Plaque-Free) and Aged (Plaque-Bearing) Tg2576 Mice" The Journal of Pharmacology and Experimental Therapeutics, vol. 305, No. 3, 2003, pp. 864-871.
Libby, "Inflammation in atherosclerosis," Nature, 420(6917):868-874 (2002).
Lim et al., "Ibuprofen Suppresses Plaque Pathology and Inflammation in a Mouse Model of Alzheimer's Disease," The Journal of Neuroscience, Aug. 1, 2000, 20(15):5709-5714.
Loeb et al., "A randomized, controlled trial of doxycycline and rifampin for patients with Alzheimer's disease," J Am Geriatr Soc, 52(3): 381-7 (2004).
Mackenzie et al., "Nonsteroidal anti-inflammatory drug use and Alzheimer-type pathology in aging," Neurology, 50(4):986-990 (1998).
Mandel, "CERE-110, an adeno-associated virus-based gene delivery vector expressing human nerve growth factor for the treatment of Alzheimer's disease," Curr Opin Mol Ther, 12(2): 240-247 (2010).
Mash et al., "Loss of M2 muscarine receptors in the cerebral cortex in Alzheimer's disease and experimental cholinergic denervation," Science, 228(4703):1115-1117 (1985).
McLaurin et al., "Cyclohexanehexol inhibitors of Aβ aggregation prevent and reverse Alzheimer phenotype in a mouse model," Nat Med, 12(7):801-808 (2006).
Mitchell et al., "Aerodynamic Particle Size Analysis of Aerosols from Pressurized Metered-Dose Inhalers: Comparison of Andersen 8-Stage Cascade Impactor, Next Generation Pharmaceutical Impactor, and Model 3321 Aerodynamic Particle Sizer Aerosol Spectrometer," AAPS PharmSciTech, 4(4): Article 54 (2003).
Mor et al., "Mast cells and atherosclerosis," Israel Med Assoc J, 3:216-221 (2001).
Morihara et al., "Ibuprofen Suppresses Interleukin-1β Induction of Pro-Amyloidogenic α1-Antichymotrypsin to Ameliorate β-Amyloid (Aβ) Pathology in Alzheimer's Models," Neuropsychopharmacology (2005) 30, 1111-1120.
Moss et al., "The absorption and clearance of disodium cromoglycate from the lung in rat, rabbit, and monkey," Toxicol Appl Pharmacol, 17(3):699-707 (1970).
Murphy, "Cromolyn sodium: basic mechanisms and clinical usage," Pediatric Asthma, Allergy, and Immunology, 2(4):237-254 (1988).
Neale et al., "The pharmacokinetics of sodium cromoglycate in man after intravenous and inhalation administration," Br J Clin Pharmacol, 22:373-382 (1986).
Netzer et al., "The actual role of sodium cromoglycate in the treatment of asthma-a critical review," Sleep Breath, 16:1027-1032 (2012).
Newman et al., "Therapeutic Aerosols 1—Physical and Practical Considerations," Thorax, 38(12): 881-886 (1983).
Notice of Allowance and Fees Due for U.S. Appl. No. 15/902,491 dated Apr. 19, 2019.
Notice of Allowance and Fees Due for U.S. Appl. No. 15/916,740 dated Apr. 26, 2019.
Obici et al., "AA amyloidosis: basic knowledge, unmet needs and future treatments, " Swiss Medical Weekly, 142:w13580 (2012).
Ono et al., "Push-pull benzothiazole derivatives as probes for detecting β-amyloid plaques in Alzheimer's brains," Bioorg Med Chem, 17(18):7002-7007 (2009).
Onodera et al., "Appropriate Administration Setting and Efficacy Evaluation in Clinical Trials (Phase I to III Clinical Trials) for the Development of New Drugs," Science & Technology Co., Ltd., 1st Edition, p. 100-101.
Palacios et al., "The pharmacological assessment of RS 86 (2-ethyl-8-methyl-2,8-diazaspiro-[4,5]-decan-1,3-dion hydrobromide). A potent, specific muscarinic acetylcholine receptor agonist," Eur J Pharmacol, 125(1):45-62 (1986).
Panza et al., "Immunotherapy for Alzheimer's Disease: From anti-b-amyloid to tau-based Immunization strategies," Immunotherapy, 4(2):213-238 (2012).
Parepally et al., "Brain uptake of nonsteroidal anti-inflammatory drugs: ibuprofen, flurbiprofen, and indomethacin," Pharm Res, 23(5):873-881 (2006).
Petersen et al., "Vitamin E and donepezil for the treatment of mild cognitive impairment," N Engl J Med, 352(23):2379-2388 (2005).
Pratico D: "Alzheimer's disease and non-steroidal anti-inflammatory drugs: Old therapeutic tools with novel mechanisms of action?", Current Medicinal Chemistry—Central Nervous System Agents, vol. 5, No. 2, pp. 111-117, 2005.
Péhourcq et al., "Diffusion of arylpropionate non-steroidal anti-inflammatory drugs into the cerebrospinal fluid: a quantitative structure-activity relationship approach," Fundam Clin Pharmacol, 18(1):65-70 (2004).
Reagan-Shaw et al., "Dose Translation from Animal to Human Studies Revisited," The FASEB, 22: 659-661 (2007).
Reverchon et al., "Production of Cromolyn Sodium Microparticles for Aerosol Delivery by Supercritical Assisted Atomization," AAPS PharmSciTech 2007; 8(4) Article 114, Dec. 21, 2007.
Richards et al., "Absorption and disposition kinetics of cromolyn sodium and the influence of inhalation technique," J Pharmacol Exp Ther, 241(3):1028-1032 (1987).
Sabbagh et al., "Latrepirdine, a potential novel treatment for Alzheimer's disease and Huntington's chorea," Curr Opin Investig Drugs, 11(1): 80-91 (2010).
Schnabel, J. "Early Results of Alzheimer's Passive Vaccine Trial Mixed," Jun. 19, 2008, http://www.dana.org/News/Details.aspx?id=42815 printed Jan. 19, 2017, pp. 1-3.
Schneider et al., "Current Alzheimer's disease clinical trials: methods and placebo outcomes," Alzheimers Dement, 5(5):388-397 (2009).
Shin et al., "Interpretation of Animal Dose and Human Equivalent Dose for Drug Development," Journal of Korean Oriental Medicine, 31: 1-7 (2010).
STN database CAS RN: 16110-51-3 (Nov. 16, 1984).
Strejan et al., "Suppression of chronic-relapsing experimental allergic encephalomyelitis in strain-13 guinea pigs by administration of liposome-associated myelin basic protein," J Neuroimmunol, 7(1):27-41 (1984).
Sun et al., "Mast cells promote atherosclerosis by releasing proinflammatory cytokines," Nat Med, 13(6):719-724 (2007).
Sun et al., "Synthesis of scyllo—inositol derivatives and their effects on amyloid beta peptide aggregation," Bioorganic & Medicinal Chemistry 16 (2008), pp. 7177-7184.
Tavemi et al., "Donepezil medicated memory improvement in traumatic brain injury during post acute rehabilitation, " Brain Inj, 12(1):77-80 (1998).
Thal et al., "A randomized, double-blind, study of rofecoxib in patients with mild cognitive impairment," Neuropsychopharmacology, 30:1204-1215 (2005).
Tronde et al., "Pulmonary absorption rate and bioavailability of drugs in vivo in rats: structure-absorption relationships and physicochemical profiling of inhaled drugs," J Pharm Sci, 92(6):1216-1233 (2003).
Upadhyaya, P. et al, "Therapy of Alzheimer's disease: An update," African Journal of Pharmacy and Pharmacology, vol. 4(6), pp. 408-421, Jun. 2010.
Veld et al., "Nonsteroidal antiinflammatory drugs and the risk of Alzheimer's disease," N Engl J Med, 345:1515-1521 (2001).
Wang et al. "Allopregnanolone reverses neurogenic and cognitive deficits in mouse model of Alzheimer's disease," PNAS, 107(14): 6498-6503 (2010).

(56) References Cited

OTHER PUBLICATIONS

Weggen et al., "A subset of NSAIDs lower amyloidogenic Aβ42 independently of cyclooxygenase activity," Nature, 414(6860):212-216 (2001).

Wettstein et al., "Clinical trials with the cholinergic drug RS 86 in Alzheimer's disease (AD) and senile dementia of the Alzheimer type (SDAT)," Psychopharmacology, 84(4):572-573 (1984).

Yan et al., "Anti-inflammatory drug therapy alters β-amyloid processing and deposition in an animal model of Alzheimer's disease," J Neurosci, 23:7504-7509 (2003).

Zhang et al., "Cromolyn Reduces Levels of the Alzheimer's Disease-Associated Amyloid β-Protein by Promoting Microglial Phagocytosis," Sci Rep, 8: Article Number: 1144 (2018).

Zhou et al., "Drug-lactose binding aspects in adhesive mixtures: controlling performance in dry powder inhaler formulations by altering lactose carrier surfaces," Adv Drug Deliv Rev, 64(3):275-284 (2012).

Zlokovic et al., "Neurovascular pathways to neurodegeneration in Alzheimer's disease and other disorders," Nat Rev Neurosci, 12(12):723-738 (2011).

\* cited by examiner

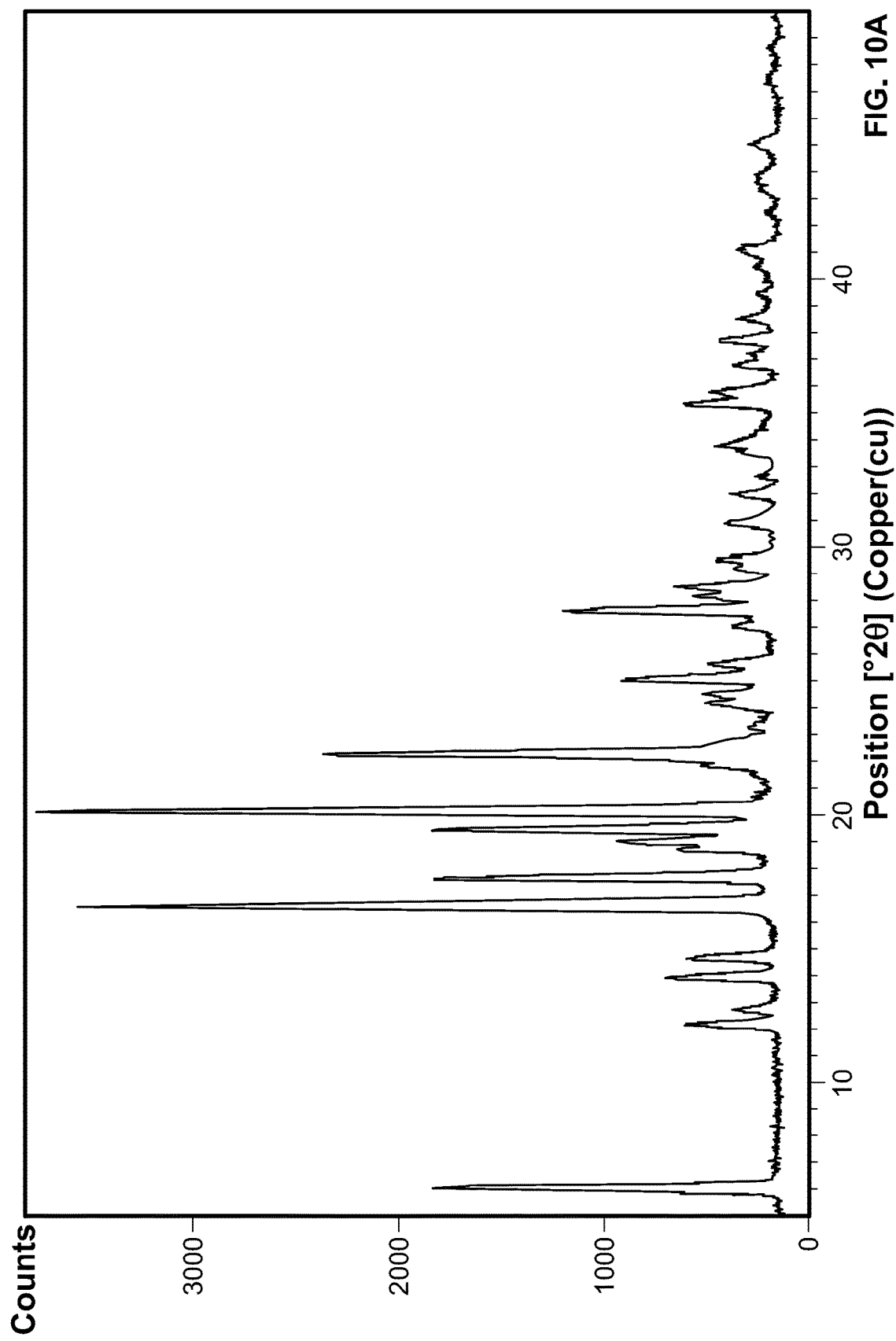

POWDERED FORMULATIONS OF CROMOLYN SODIUM AND IBUPROFEN

CROSS-REFERENCE TO RELATED APPLICATIONS

This application claims priority to and the benefit of U.S. Provisional Patent Application Ser. No. 62/534,848, filed Jul. 20, 2017.

BACKGROUND OF THE INVENTION

Therapies to prevent Alzheimer's Disease (AD) progression remain a high-unmet medical need. US Food and Drug Administration (FDA) approved acetylcholinesterase (AChE) inhibitor drugs, such as donepezil, rivastigamine and galantamine are indicated for symptomatic relief in persons with mild to moderate AD (Cummings J L, "Alzheimer's disease," *N Engl J Med* (2004) 351, 56-67; Knowles J, "Donepezil in Alzheimer's disease: an evidence-based review of its impact on clinical and economic outcomes," *Core Evidence* (2006) 1, 195-219). These drugs increase levels of available acetylcholine during synaptic transmission and thus compensate for the diminished function of cholinergic neurons. However, none of the drugs approved for AD are disease-modifying treatments that affect the underlying pathophysiology of the disease, so the duration of their benefit is short-term (Knowles, 2006). The development of successful disease-modifying treatments, in contrast, would have a long-term beneficial outcome on the course of AD progression.

The treatment of AD will require addressing the multiple triggers of pathogenesis. There are two primary neuropathologies in the brains of AD patients: i) extracellular protein plaques principally composed of Aβ peptides, also known as amyloid plaques; and ii) intracellular tangles of fibrils composed of tau protein found inside of neurons, also known as tau tangles. The advent and spread of neurotoxic oligomeric aggregates of Aβ is widely regarded as the key trigger leading to neuronal damage, which then leads to the accumulation of intracellular tau tangles, and finally to neuronal cell death in AD pathogenesis.

Beta-amyloid peptides (37 to 43 amino acids in length) are formed by sequential cleavage of the native amyloid precursor protein (APP) (Karran et al., "The amyloid cascade hypothesis for Alzheimer's disease: an appraisal for the development of therapeutics," *Nature Reviews* (2011) 10, 698-712). Aberrant Aβ peptide isoforms that are 40 or 42 amino acids in length (Aβ 40 and 42) misfold into aggregates of oligomers that grow into fibrils that accumulate in the brain as amyloid plaques. More importantly for AD pathogenesis, the alternate fate of Aβ oligomers is to become trapped in neuronal synapses where they hamper synaptic transmission, which eventually results in neuronal degeneration and death (Haass et al., "Soluble protein oligomers in neurodegeneration: lessons from the Alzheimer's amyloid β-peptide," *Nature Reviews Mol. Cell Biol.* (2007) 8:101-112; Hashimoto et al, "Apolipoprotein E, especially apolipoprotein E4, increases the oligomerization of amyloid beta Peptide," *J. Neurosci.* (2012) 32, 15181-15192).

The cascade of Aβ oligomer-mediated neuronal intoxication is exacerbated by another AD trigger: chronic local inflammatory responses in the brain (Krstic et al., "Deciphering the mechanism underlying late-onset Alzheimer disease," *Nature Reviews Neurology* (2013), Jan. 9 (1): 25-34). Alzheimer's disease has a chronic neuro-inflammatory component that is characterized by the presence of abundant microglial cells associated with amyloid plaque. (Heneka et al., "Acute treatment with the PPARγ agonist pioglitazone and ibuprofen reduces glial inflammation and Abeta1-42 levels in APPV717I transgenic mice," Brain (2005) 128, 1442-1453; Imbimbo et al., "Are NSAIDs useful to treat Alzheimer's disease or mild cognitive impairment," *Front. Aging Neurosci* (2010) 2 (article 19), 1-14). These cyclooxygenase (COX1/COX2)-expressing microglia, which phagocytose amyloid oligomers, become activated to secrete pro-inflammatory cytokines. (Hoozemans et al., "Soothing the inflamed brain: effect of non-steroidal anti-inflammatory drugs on Alzheimer's disease pathology," *CNS & Neurological Disorders—Drug Targets* (2011) 10, 57-67; Griffin T S., "What causes Alzheimer's" *The Scientist* (2011) 25, 36-40; Krstic 2013). This neuro-inflammatory response, besides promoting local vascular leakage through the blood brain barrier (BBB). Zlokovic (Zlokovic B., "Neurovascular pathways to neurodegeneration in Alzheimer's disease and other disorders," *Nature Reviews Neurosci.* (2011) 12, 723-738) has been implicated in driving further production of aberrant Aβ peptides 40 and 42 via modulation of gamma-secretase activity (Yan et al., "Anti-inflammatory drug therapy alters β-amyloid processing and deposition in an animal model of Alzheimer's disease," *J. Neurosci.* (2003) 23, 7504-7509; Karran 2011) and to be detrimental to hippocampal neurogenesis in the adult brain (Gaparini et al., "Non-steroidal anti-inflammatory drugs (NSAIDs) in Alzheimer's disease: old and new mechanisms of action," *J. Neurochem* (2004) 91, 521-536). Thus, neuro-inflammation, in combination with amyloid oligomer-mediated neuronal intoxication, creates a cycle that results in progressive neural dysfunction and neuronal cell death spreading throughout the brain in subjects with AD.

Compelling evidence from multiple epidemiology studies revealed that long-term dosing with non-steroidal anti-inflammatory drugs (NSAIDs) dramatically reduced AD risk in the elderly, including delayed disease onset, reduced symptomatic severity and slowed cognitive decline. (Veld et al., "Nonsteroidal anti-inflammatory drugs and the risk of Alzheimer's disease," *N. Engl. J. Med* (2001) 345, 1515-1521; Etminan et al., "Effect of non-steroidal anti-inflammatory drugs on risk of Alzheimer's disease: systematic review and meta-analysis of observational studies," *Brit. Med. Journal* (2003) 327, 1-5; Imbimbo, 2010). Three mechanisms have been proposed for how NSAIDs inhibit the processes that contribute to AD progression: i) by inhibiting COX activity to reduce or prevent microglial activation and cytokine production in the brain (Mackenzie, et al., "Nonsteroidal anti-inflammatory drug use and Alzheimer-type pathology in aging." *Neurology* (1998) 50, 986-990; Alafuzoff et al., "Lower counts of astroglia and activated microglia in patients with Alzheimer's disease with regular use of non-steroidal anti-inflammatory drugs," *J. Alz. Dis.* (2000) 2, 37-46; Yan, 2003; Gasparini, 2004; Imbimbo, 2010); ii) by reducing amyloid deposition (Weggen et al., "A subset of NSAIDs lower amyloidogenic Abeta42 independently of cyclooxygenase activity," *Nature* (2001) 414, 212-216; Yan, 2003; Imbimbo, 2010); or iii) by blocking COX-mediated prostaglandin E2 responses in synapses (Kotilinek et al., "Cyclooxygenase-2 inhibition improves amyloid-β-mediated suppression of memory and synaptic plasticity," *Brain* (2008) 131, 651-664.

Therefore, NSAIDs are predicted to dampen the neuro-inflammatory response and impact AD progression via several mechanisms. When administered together with drugs that inhibit Aβ oligomerization, the combination treatment paradigm is proposed to attenuate the multiple triggers leading to neurodegeneration and neuronal death. The decline in cognitive performance may be reversed, due to neuronal plasticity and neurogenesis in the hippocampus (Kohman et al., "Neurogenesis, inflammation and behavior," *Brain, Behavior, and Immunity* (2013) 27, 22-32), if AD progression is arrested at a very early stage.

SUMMARY OF THE INVENTION

The invention encompasses a composition comprising cromolyn sodium and ibuprofen, wherein the cromolyn sodium is micronized and the cromolyn sodium and ibuprofen are present in a weight ratio of 1:1-2. In one embodiment, the ibuprofen is passed through a sieve, such as a 300 µm sieve.

The invention also encompasses methods of making a composition of cromolyn sodium and ibuprofen comprising micronizing cromolyn sodium; separately sieving cromolyn sodium and ibuprofen; blending sieved cromolyn sodium and ibuprofen; and blend co-milling the blended cromolyn sodium and ibuprofen. In one embodiment, the sieve is about 250 µm to 500 µm sieve. In another embodiment, the micronizing step is performed at a feed gas pressure of about 45 psi and a grinding pressure of about 45 psi.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 10A illustrates a powdered x-ray diffraction pattern for Batch 1.

DETAILED DESCRIPTION OF THE PRESENT INVENTION

Figure 1:
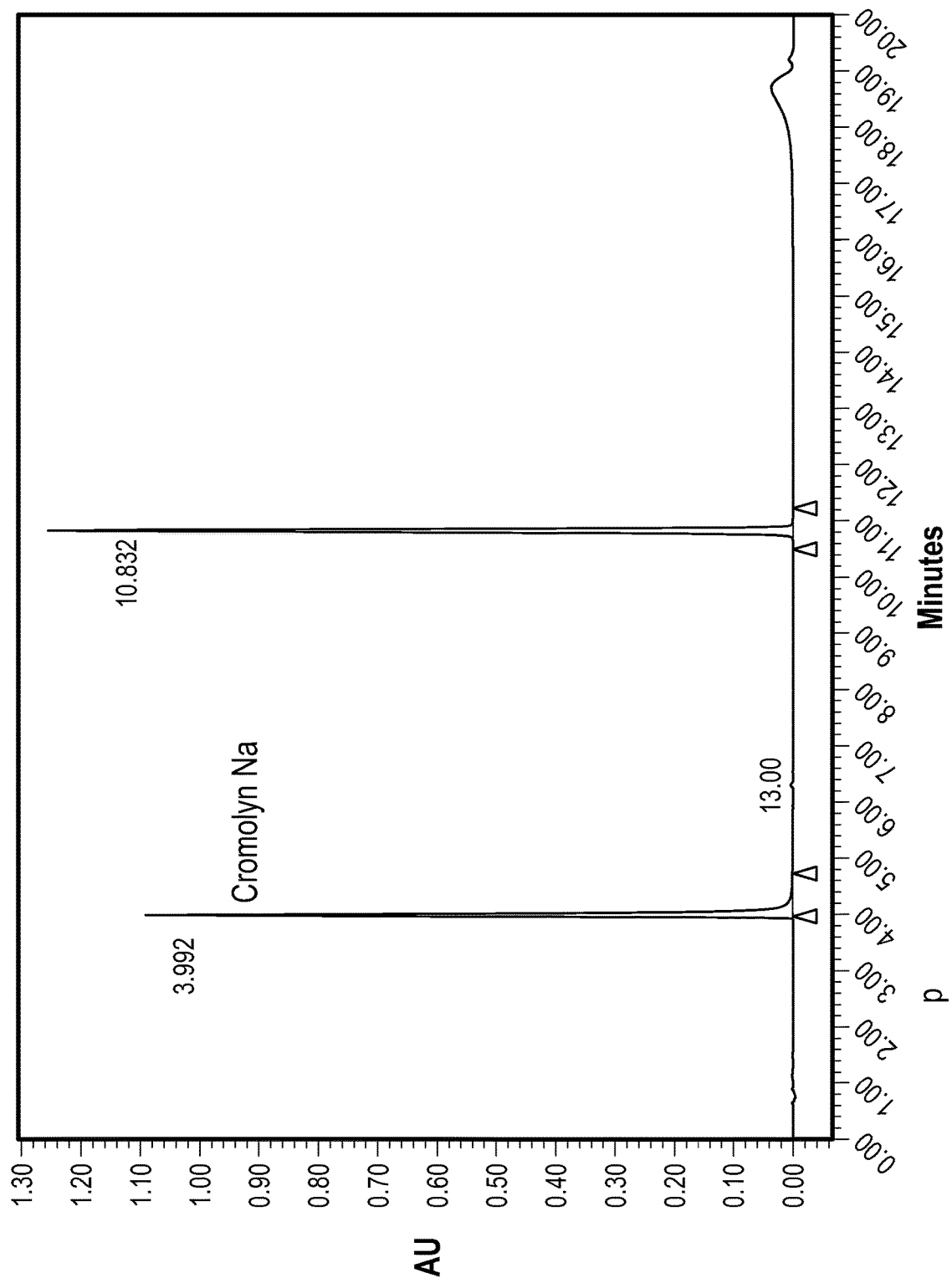
FIG. 1 illustrates an HPLC chromatogram of a sample containing cromolyn sodium and ibuprofen, where cromolyn sodium has a peak at 3.99 and ibuprofen has a peak at 10.83.

The invention encompasses compositions for a dosage form via inhalation. Basically, the invention combines at least two pharmaceutically active ingredients, both in powdered form, for administration via inhalation. The compositions can be used in formulations to enable easy dosing for patients, in contrast to dosing each API separately such as where one is inhaled and the other taken orally. An advantage of the simultaneous dosing of two APIs via inhalation is greater patient compliance with drug administration.

In particular, the invention is applicable for patients with diseases that impair mental performance, such as Alzheimer's disease, where the patient may have difficulty remembering to administer their medications. The invention is also applicable when the disease impacts physical activity, such as difficulty grasping pills or even the act of swallowing. The inability to correctly administer a dosage form can diminish the effect of the medication. These difficulties can exacerbate the disease because drug(s) administration is difficult, inconsistent, and/or under-dosed. To address these problems and increase patient compliance and ease administration, the present invention provides a combined dosage form suitable for administration via inhalation to treat Alzheimer's disease and other neurological diseases. Because of its versatility, the composition and formulation may also be used to treat other diseases including, but not limited to, stroke, amyotrophic lateral sclerosis (ALS), Parkinson's disease, and asthma.

One application of the present invention is a composition of cromolyn sodium and ibuprofen each in powdered form suitable for inhalation as a combination dosage form. In this case, each ingredient is in powdered form to facilitate administration via inhalation and to enable easy and accurate dosing. The invention is based in part upon the discovery that when cromolyn sodium and ibuprofen are both in powdered form, ibuprofen improves the aerodynamic flow of cromolyn. One advantage of this improvement allows for a higher concentration of cromolyn to reach deeper within the patient's lungs thereby achieving a therapeutic effect with less drug. Another advantage is that a perfect dosage via inhalation may not be necessary to achieve adequate therapeutic effect. In patients with impaired physical abilities (which may be due to a disease such as Alzheimer's disease) a perfect inhalation (a perfect "puff") may not always be possible; with the present invention, even impaired inhalation (an imperfect "puff") will deliver sufficient drug dosage to treat the desired disease. The advantages of the present composition can be applied to other diseases with similar problems and expand the list of indications where the improved dosage form may be applicable.

In one application, the co-administration of the composition of cromolyn sodium and ibuprofen can be used for the treatment of certain neurological diseases. The neurological diseases include, but are not limited to, AD, ALS, Parkinson's disease, and the effects from stroke.

The invention relied on a methods to analytically discriminate between two APIs in a single sample to evaluate the characteristics of ibuprofen to understand the influences ibuprofen can have on the formulation. The analytical methods to discriminate between the two APIs in a sample also allowed investigation of the effect of micronization of ibuprofen for inhalation. These methods allowed determination of the feasibility of cromolyn sodium and ibuprofen as a combined single dosed product. Further methods allowed determination of the compatibility of the combined APIs in the combination dosage form. We discuss each in turn.

To determine the appropriate combination dosage, an analytical method was developed to distinguish between cromolyn sodium and ibuprofen within the same sample. The method included an assay to identify and quantify each API and measure the performance of each compound by testing the emitted dose and aerodynamic particle size.

The method comprises submitting a sample having cromolyn and ibuprofen through two chromatographic columns in sequence having a first and a second mobile phase, wherein the first mobile phase has sodium acetate with a buffer pH of about 5.5 and methanol, and the second mobile phase perchloric acid and acetonitrile, and detecting the cromolyn and ibuprofen. The sequence of columns and mobile phases are interchangeable. For instance, regarding mobile phases the terms first and second are used to demonstrate different mobile phases, not their sequence. The chromatographic columns include, but are not limited to, Agilent Poroshell 120 SB-C18 100×3 mm, 2.7µ. The mobile phases are present in an elution gradient of about 70:30 to 3:97 by volume, preferably from about 75:25 to 5:95, and more preferably from about 80:20 to 10:90 by volume. Any know method of detection may be used in the method including, but not limited to, UV, preferably the detection is carried out by UV.

In one embodiment of the analytical method, the HPLC analytical method used two columns: (1) Phenomenex Hyperclone BDS C18 130A 250×4.6 mm, 5µ and (2) Zorbax SB C18 150×4.6 mm, 3.5µ. The mobile phases included a sodium acetate or potassium phosphate and methanol mixture for cromolyn sodium and a perchloric acid:acetonitrile mixture for ibuprofen. For instance, in one example 23 nM sodium acetate buffer (pH 5.5):methanol was used for cromolyn sodium and 0.2% perchloric acid:acetonitrile for ibuprofen. The mobile phase for cromolyn can have a pH of about 4 to about 7.5, preferably from about 4.5 to about 7, and more preferably from about 5.5 to 6.8.

The analytical method used a gradient system of 85:15 to 10:90 (v/v) to assess the elution of both APIs. The wavelength of detection (both used for the detection of each API) was as follows: cromolyn sodium—254 nm and ibuprofen—214 nm.

The injection volume was changed from 100 µL to 10 µL; the run time was changed from 20 to 5 minutes; and the gradient was changed from 85:15-10:90 (v/v) to 80:20-10:90.

Figure 2:
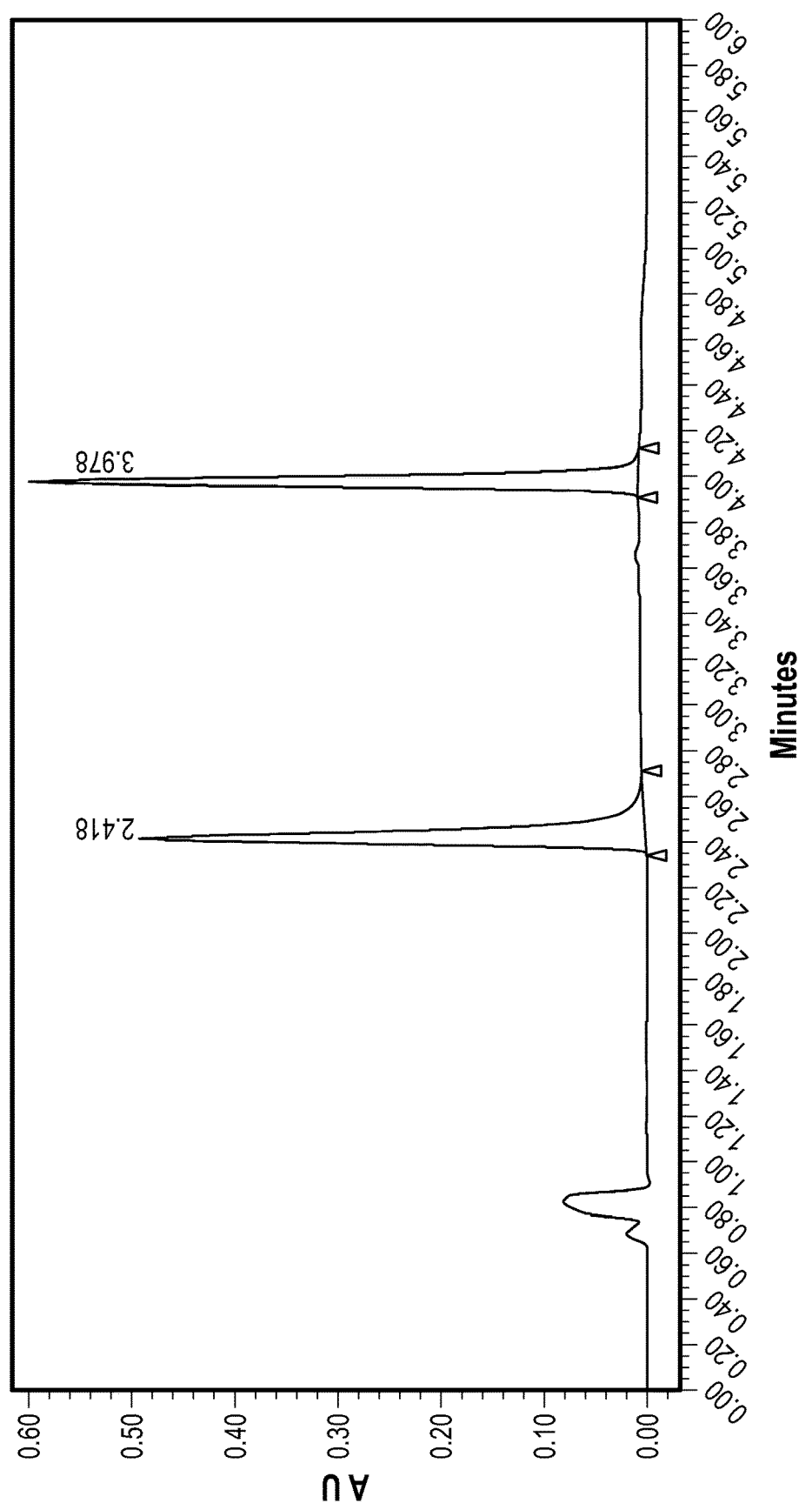
FIG. 2 illustrates an HPLC chromatogram of a sample containing cromolyn sodium and ibuprofen, where cromolyn sodium has a peak at 2.42 and ibuprofen has a peak at 3.98.

The analytical method is exemplified in Example 1 and Example 2. Cromolyn sodium and ibuprofen separated well, as illustrated in FIG. 1 and FIG. 2. Cromolyn sodium was detected at 3.99 minutes and ibuprofen was detected at 10.83 minutes. After achieving distinct signals, the method was optimized resulting in a shortened retention time of 2.418 minutes for Cromolyn and 3.978 minutes for Ibuprofen.

The ibuprofen used in the composition for the formulation may be in coarse or micronized form or any other form, as long as that form is suitable for inhalation. Another prerequisite is that the ibuprofen combines well with cromolyn sodium in order to enhance the delivery of cromolyn sodium via inhalation. In particular, the combination should deliver cromolyn sodium to the deep parts of the lung, e.g., DPI 4moc (stage 4 to MOC, representing the area of the lung consisting of the secondary bronchi to the alveoli).

Ibuprofen was characterized to determine the parameters necessary to administer a therapeutically effective amount using an inhalation delivery system. The methodology included particle size determination (PSD); powdered x-ray crystallization diffraction (PXRD); and gravimetric vapor sorption (GVS). The methods determined that coarse ibuprofen was crystalline and non-hygroscopic. The results are summarized in Example 3. Ibuprofen adsorption-desorption isotherm showed <0.2% weight gain upon exposure to moisture suggesting that ibuprofen is non-hydroscopic.

The invention also encompasses a composition having micronized ibuprofen, where the ibuprofen has a size parameter of about ≤10 μm; however, particle size may also include ≤5 μm. The micronization may be performed on coarse ibuprofen using an air-jet mill or similar apparatus, such as a grinder or a mill. Other methods to micronize the ibuprofen include milling, bashing, cutting, or crushing. For example, two batches were micronized with an air-jet mill using a feed gas pressure of about 45 psi and a grinding pressure of about 45 psi. One batch was micronized a second time under the same conditions. Optionally, the ibuprofen may be micronized more than once. After micronization, particle size distribution was performed on the micronized ibuprofen by wet dispersion. The micronized ibuprofen was highly soluble in organic solvents; not dispersible in water (formed agglomerates); and soluble in different surfactants containing aqueous media even at low concentrations of the surfactant. Example 3 illustrates the process and results of ibuprofen micronization.

Micronized ibuprofen adsorbed higher moisture of ~3% by weight on the surface compared to <0.2% adsorption by coarse ibuprofen. The adsorption increase was due to the increased surface area upon micronization and generation of surface amorphous material. See FIGS. 11A, 11B, and 11C. A diluent and a stabilizer may be necessary for product performance and stability purposes. A cromolyn stabilizer is magnesium stearate and the use of a diluent such as lactose, which optionally may be used in the composition of the formulation.

Cromolyn used in the composition formulation may primarily be manufactured for inhalation. Generally, the cromolyn is micronized. The cromolyn micronization produces an ultra-fine powder (d<10 μm) of small particle size. Micronized Cromolyn typically has a specification of d(90%)≤5 μm.

The invention also encompasses a composition of cromolyn sodium and ibuprofen for delivery via inhalation. This composition comprises micronized cromolyn sodium and ibuprofen, wherein the ibuprofen may or may not be micronized, i.e., the ibuprofen may be coarse or micronized. The composition improves the delivery of cromolyn, from cromolyn only compositions or where cromolyn is delivered in sequence (not simultaneously) with ibuprofen. For instance, the inhaled formulation of cromolyn only can deliver a therapeutically effective amount of cromolyn to the deep lung of about 23% to about 29% of the dosed amount. In contrast, it was found that the composition of the present invention delivered a therapeutically effective amount of cromolyn in a range of about 34% to about 53% and preferably 35% to about 44% of the dosed amount One composition of the invention comprises 17.1 mg of cromolyn and 10 mg of ibuprofen. This is in alignment with current study drug concentrations being utilized in clinical studies. As used herein, unless otherwise indicated, the term "cromolyn" includes cromolyn, cromolyn sodium, and other forms of pharmaceutically acceptable salts of cromolyn.

Formulation 1A

| Component | Function | % w/w | mg/capsule |
|---|---|---|---|
| Cromolyn sodium | Active Ingredient | 58.0 | 17.1 (±1.7) |
| Lactose Monohydrate | Diluent | 40.0 | 12.8 (±0.64) |
| Magnesium stearate (micronized) | Stabilizer | 2.0 | 0.6 (±0.03) |
| | | 100 | 32.0 (±2.4) |

Formulation 2A—Cromolyn with Coarse Ibuprofen

| Component | Function | % w/w | mg/capsule |
|---|---|---|---|
| Cromolyn sodium | Active Ingredient | ~62 | 17.1 (±1.7) |
| Ibuprofen (coarse) | Active Ingredient | ~36 | 10.0 (±1.0) |
| Magnesium stearate (micronized) | Stabilizer | 2 | 0.54 (±0.027) |
| | | | 27.64 (±1.9) |

Formulation 2B—Cromolyn with Micronized Ibuprofen

| Component | Function | w/Diluent | | w/o Diluent | |
|---|---|---|---|---|---|
| | | % w/w | mg/capsule | % w/w | mg/capsule |
| Cromolyn sodium | Active Ingredient | ~36.6 | 17.1 ((±1.7) | ~62 | 17.1 ((±1.7) |
| Ibuprofen (micronized) | Active Ingredient | ~21.4 | 10.0 (±1.0) | ~36 | 10.0 (±1.0) |
| Lactose Monohydrate | Diluent | ~40.0 | 18.7 (±0.9) | — | — |
| Magnesium stearate (micronized) | Stabilizer | 2.0 | 0.9 | 2.0 | 0.54 (±0.027) |
| | | 100 | 46.7 (±3.5) | | 27.64 (±1.9) |

In one formulation, both cromolyn sodium and ibuprofen are passed through a sieve. The sieve size may be from about 600 µm to about 200 µm, preferably from about 500 µm to about 250 µm, and more preferably from about 300 µm to 400 µm. Typically, the weight ratio of cromolyn sodium to ibuprofen is about 1:1 to about 1:2.5, preferably, from about 1:1.1 to about 1:2, and more preferably from about 1.1:1.7. Optionally, the formulation includes pharmaceutically acceptable excipients, such as magnesium stearate and lactose monohydrate.

The stability of the composition of cromolyn sodium and ibuprofen is exemplified in Example 5. The formulations using either micronized ibuprofen or coarse ibuprofen provided sufficient performance of an inhaled substance when compared to the specifications of the cromolyn only product. The formulation enhanced the aerodynamic performance of cromolyn sodium during inhalation by comparison to a formulation of cromolyn sodium, lactose, and magnesium stearate. The combination product batches had a comparable emitted dose as the six clinical batches produced of the cromolyn only product. The six batch formulations manufactured with cromolyn and excipients only had a mean of 34.97% of the product reaching the deep lung area based on the NGI test results summation of Stage 3-MOC whereas with combination of cromolyn using either course or micronized ibuprofen had a mean result of 46% of the inhaled cromolyn reaching the deep lung area. Therefore, the compositions of the invention include cromolyn and ibuprofen compositions having a mean result of 36% to 56%, preferably from about 41% to about 51%, and more preferably from about 43% to about 48% of the inhaled cromolyn reaching the deep lung area. As used herein, unless otherwise defined, the term “lung area” refers to Stage 3-MOC. The stability study performed under accelerated conditions showed no effect of the APIs towards each other.

TABLE 1

NGI comparison of Ibuprofen - Cromolyn/Ibuprofen$_{micronized}$ vs Cromolyn/Ibuprofen$_{coarse}$

| | Feasibility Batches (Cromolyn w/Ibuprofen) % of Ibuprofen Dose[1] | | | |
|---|---|---|---|---|
| Location | AFC05 Ibuprofen$_{Micronized}$ w/MgSt[2] | AFC06 Ibuprofen$_{Micronized}$ w/o MgSt[2] | AFC09 Ibuprofen$_{coarse}$ w/MgSt[2] | AFC10 Ibuprofen$_{coarse}$ w/o MgSt[2] |
| Stage 1 -Mouth | 6.5 | 6.4 | 59.9 | 64.5 |
| Stage 2- Pharynx | 18.9 | 20.7 | 11.1 | 5.9 |
| Stage 3 - Trachea/Primary Branch | 18.2 | 18.5 | 1.7 | 1.7 |
| Stage 4 - Secondary Bronchi | 12.4 | 11.4 | 0.9 | 0.8 |
| Stage 5 - Terminal Branch | 3.6 | 2.8 | 0 | 0 |
| Stage 6&7 - Alveoli | 1.5 | 0.7 | 0 | 0 |

[1]All batches used micronized Cromolyn sodium API

[2]MgSt—Magnesium Stearate

3 - Cromolyn with Lactose monohydrate and Magnesium stearate

TABLE 2

NGI comparison of Cromolyn - Cromolyn/Ibuprofen$_{micronized}$
vs Cromolyn/Ibuprofen$_{coarse}$ vs. Cromolyn Only[3]

Feasibility Batches (Cromolyn w/Ibuprofen vs Cromolyn Only)
% of Cromolyn Dose[1]

| Location | AFC05 Ibuprofen$_{Micronized}$ w/MgSt[2] | AFC06 Ibuprofen$_{Micronized}$ w/o MgSt[2] | AFC09 Ibuprofen$_{coarse}$ w/MgSt[2] | AFC10 Ibuprofen$_{coarse}$ w/o MgSt[2] | 13PM792-PG67 Cromolyn Only[3] |
|---|---|---|---|---|---|
| Stage 1 -Mouth | 6.9 | 7.1 | 15.5 | 16.3 | 11.1 |
| Stage 2- Pharynx | 21.8 | 24.3 | 9.4 | 7.1 | 21.1 |
| Stage 3 - Trachea/Primary Branch | 20.5 | 20.6 | 12.7 | 13.0 | 19.4 |
| Stage 4 - Secondary Bronchi | 10.1 | 10.5 | 11.6 | 15.7 | 15.4 |
| Stage 5 - Terminal Branch | 3.4 | 2.9 | 7.2 | 9.2 | 7.8 |
| Stage 6&7 - Alveoli | 1.7[4] | 1.7[4] | 4.9 | 4.9 | 3.3 |

[1]All batches used micronized Cromolyn sodium API
[2]MgSt—Magnesium Stearate
[3]Cromolyn with Lactose monohydrate and Magnesium stearate
[4]With addition of Lactose Monohydrate this will improve the performance Pharmaceutically acceptable excipients for dry powdered inhalers include, but are not limited to, lactose monohydrate and magnesium stearate.

The invention encompasses methods of making the described compositions comprising micronizing ibuprofen; separately sieving cromolyn sodium and ibuprofen; blending sieved cromolyn sodium and sieved ibuprofen; and blend co-milling the blended cromolyn sodium and ibuprofen to obtain the composition.

The ibuprofen micronization step can be carried out using standard equipment commonly used in the pharmaceutical arts. The feed pressure and grinding pressure are about 30 psi to about 60 psi, preferably about 35 psi to about 50 psi, and more preferably about 45 psi. The blending step comprises blending both ingredients for a time of about 5 minutes to about 20 minutes and preferably about 10 minutes to about 15 minutes, and more preferably for about 10 minutes. The blending rate is about 35 rpm to about 60 rpm, preferably about 40 rpm to about 50 rpm, and more preferably about 49 rpm. The blend co-milling step may be blended in a single pass. The feed pressure and grinding pressure for the co-milling step are about 30 psi to about 60 psi, preferably about 35 psi to about 50 psi, and more preferably about 45 psi. Examples 4 and 5 demonstrate the method of making the formulation.

While certain features of the invention were illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLES

Example 1: Detection of Cromolyn Sodium and Ibuprofen in Same Sample

Two columns were used in the method: (1) Phenomenex Hyperclone BDS C18 130A 250×4.6 mm, 5µ and (2) Zorbax SB C18 150×4.6 mm, 3.5µ. The mobile phases were as follows: cromolyn sodium:23 nM sodium acetate buffer pH 5.5:methanol and ibuprofen:0.2% perchloric acid:acetonitrile. The mobile phases used a gradient system from 85:15 to 10:90 to assess the elution of both APIs. The wavelength used to detect each API was 254 nm for cromolyn sodium and 214 nm for ibuprofen. Table 1 summarizes the method parameters and FIG. 1 illustrates the results.

TABLE 3

Method Parameters

| Parameter | Value |
|---|---|
| Column | Agelent Poroshell 120 SB-C18 100 × 3 mm, 2.7µ |
| Column temperature | 40° C. |
| Injection Volume | 10 µL |
| Flow | 0.7 mL/min. |
| Wavelength | 214 nm |
| Run time | 20 minutes |
| Diluent | 25 mM Potassium phosphate pH 6.8:Methanol (1:1) |

Example 2: Detection of Cromolyn Sodium and Ibuprofen in Sample

The method described in Example 1 was repeated using the method parameters described in Table 4. The results are illustrated in FIG. 2.

TABLE 4

Method Parameters

| Parameter | Value |
|---|---|
| Column | Agelent Poroshell 120 SB-C18 100 × 3 mm, 2.7µ |
| Column temperature | 40° C. |
| Injection Volume | 100 µL |
| Mobile Phase | 0.2% perchloric acid:acetonitrile |
| Gradient run | |
| 0-2 min. | 80:20-10:90 |
| 2-2.1 min. | 10:90-80:20 |
| 2.1-5 min. | 80:20 |
| Flow | 0.7 mL/min. |
| Wavelength | 214 nm |
| Run time | 5 minutes |
| Diluent | 25 mM Potassium phosphate pH 6.8:Methanol (1:1) |

Using the method described in Table 4, the analysis was repeated using a 50 µg/mL standard. Table 5 summarizes the results.

TABLE 3

System Repeatability

| Injection # | Area (μV · sec) | |
|---|---|---|
| | Cromolyn | Ibuprofen |
| 1 | 1988124 | 1775569 |
| 2 | 1992850 | 1777595 |
| 3 | 1992853 | 1775814 |
| 4 | 1993644 | 1777975 |
| 5 | 1994323 | 1775675 |
| 6 | 1996294 | 1773172 |
| mean | 1993015 | 1775967 |
| % RSD | 0.1 | 0.1 |

Figure 3:
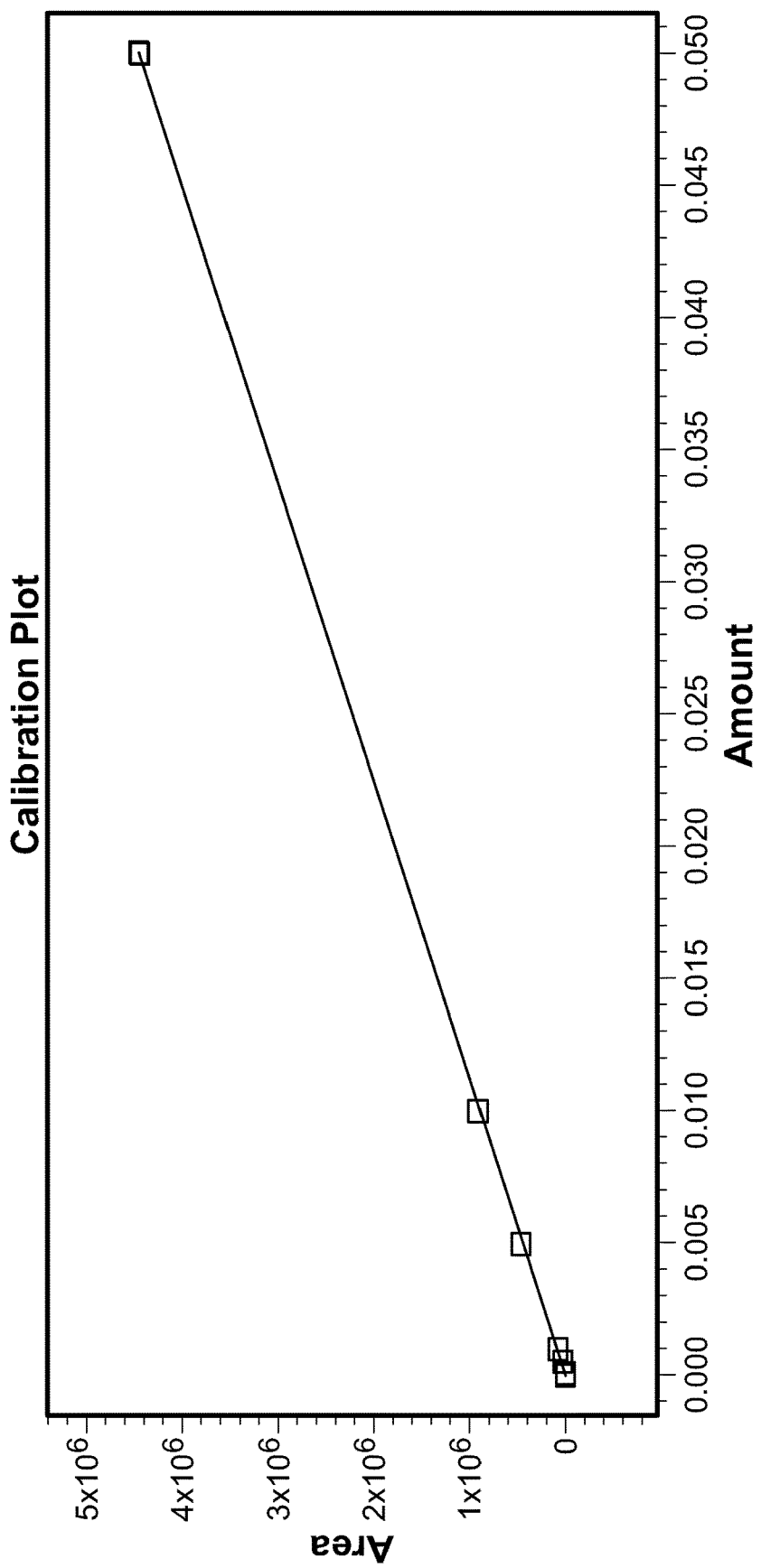
FIG. 3 illustrates a calibration plot for cromolyn sodium over the range of 0.05 to 50 µg/mL.
Figure 4:
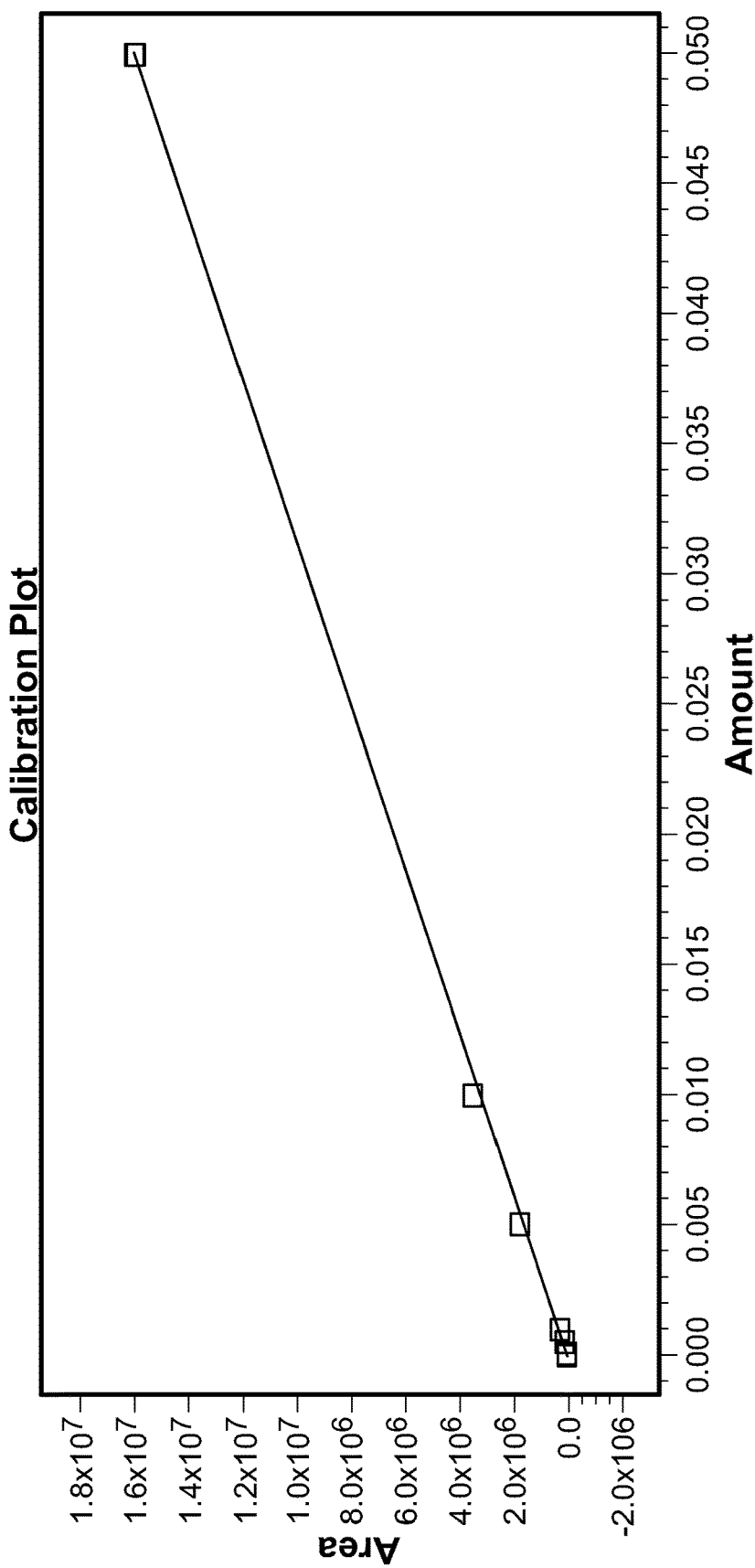
FIG. 4 illustrates a calibration plot of ibuprofen over the range of 0.05 to 50 µg/mL.

Based on the data of Table 3, the linearity was calculated for cromolyn sodium and ibuprofen over the range of 0.05-50 g/mL. FIGS. 3 and 4 illustrate the data for cromolyn sodium and ibuprofen calibration plot, respectively.

Example 3: Physical Characterization of Ibuprofen

Coarse ibuprofen was characterized using PSD, PXRD, and GVS. The tests demonstrated that coarse ibuprofen was crystalline and non-hydroscopic. Table 6 illustrates the effect of the dispersant.

TABLE 6

Effect of Dispersant

| T (Day) | D10 (μm) | D50 (μm) | D90 (μm) |
|---|---|---|---|
| 0 | 22.586 | 57.693 | 108.743 |
| 1 | 22.401 | 57.611 | 108.724 |

Figure 5:
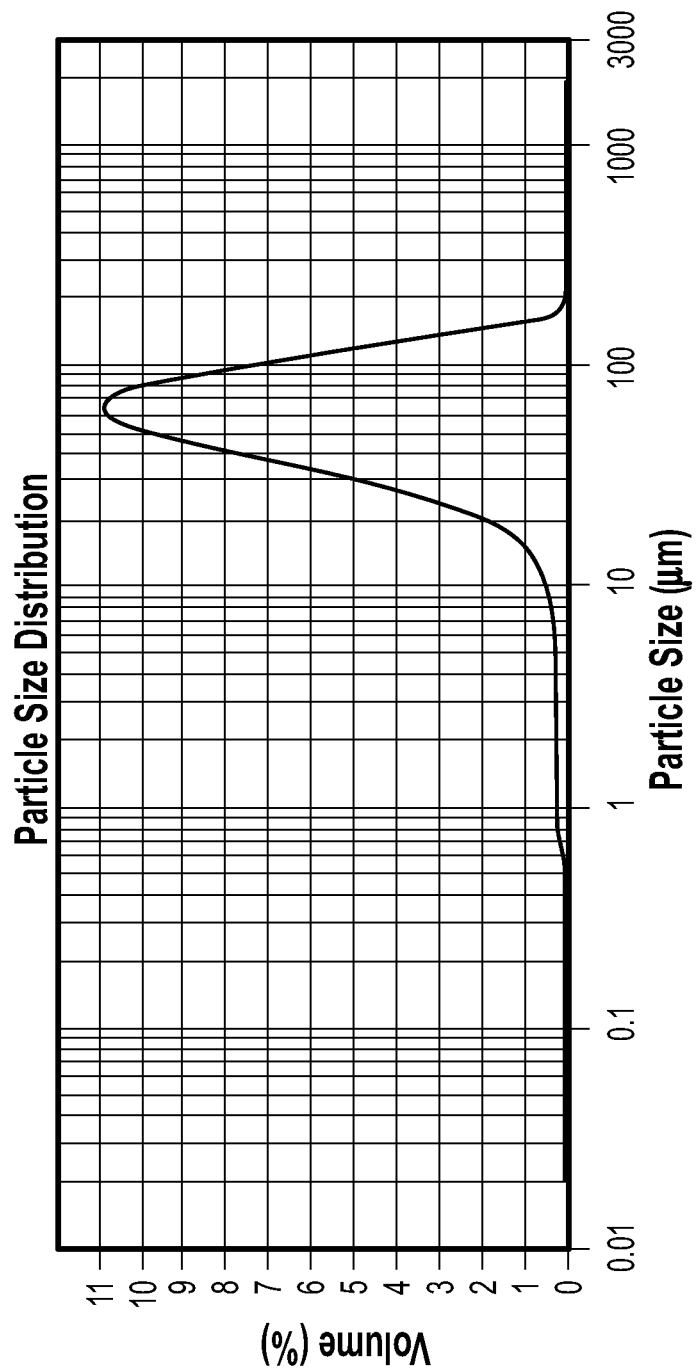
FIG. 5 illustrates a particle size distribution plot of coarse ibuprofen.

The average particle size determinations are illustrated in FIG. 5. The parameters and results were as follows: concentration 0.0406% Vol; span 1.493; uniformity 0.459; specific surface area 0.239 $m^2/g$; surface weighted mean D[2,3] 25.136 μm; and vol. weighted mean D[4,3] 62.020 μm.

Figure 6:
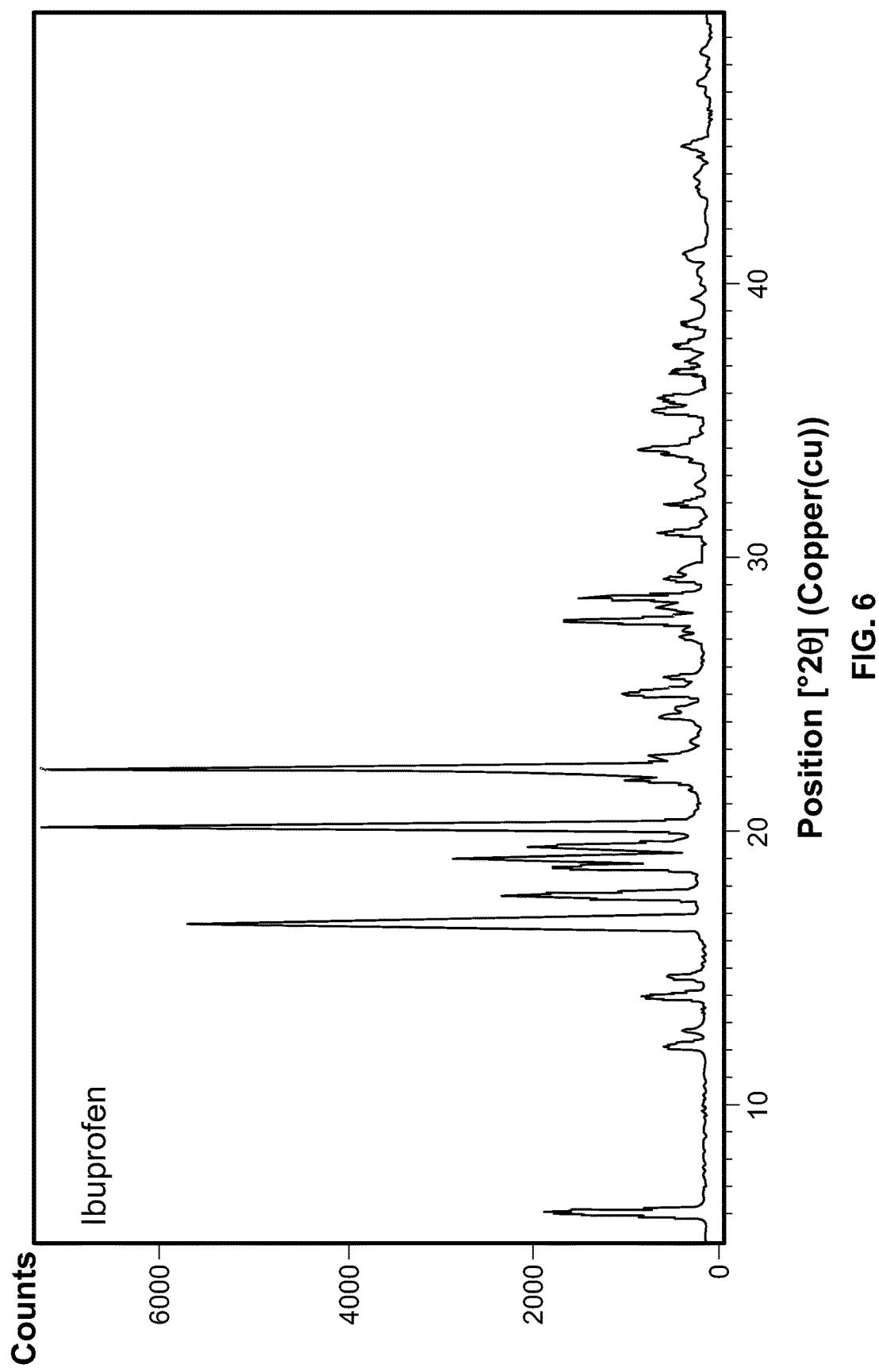
FIG. 6 illustrates a powdered x-ray diffraction pattern for coarse ibuprofen.
Figure 7:
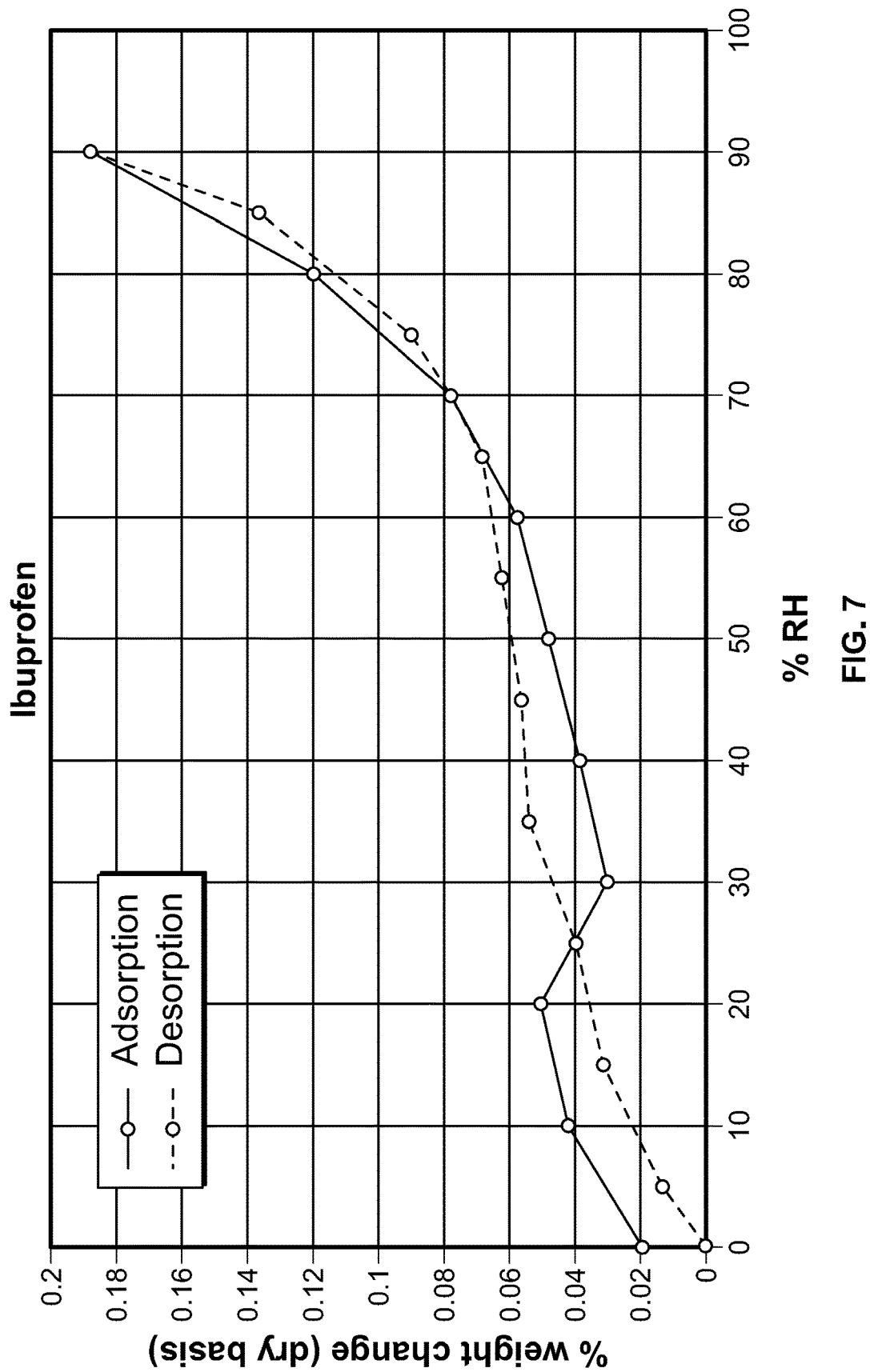
FIG. 7 illustrates a GVS plot of coarse ibuprofen.

FIG. 6 illustrates the PXRD and FIG. 7 illustrates the GVS of coarse ibuprofen. The ibuprofen adsorption-desorption isotherm showed <0.2% weight gain upon exposure to moisture, suggesting that the ibuprofen was non-hydroscopic.

Subsequently, two batches of coarse ibuprofen were micronized using an air-jet mill at feed gas pressure of 45 psi and a grinding pressure of 45 psi. Batch 1 was micronized by a single pass and Batch 2 was passed twice.

Figure 8A:
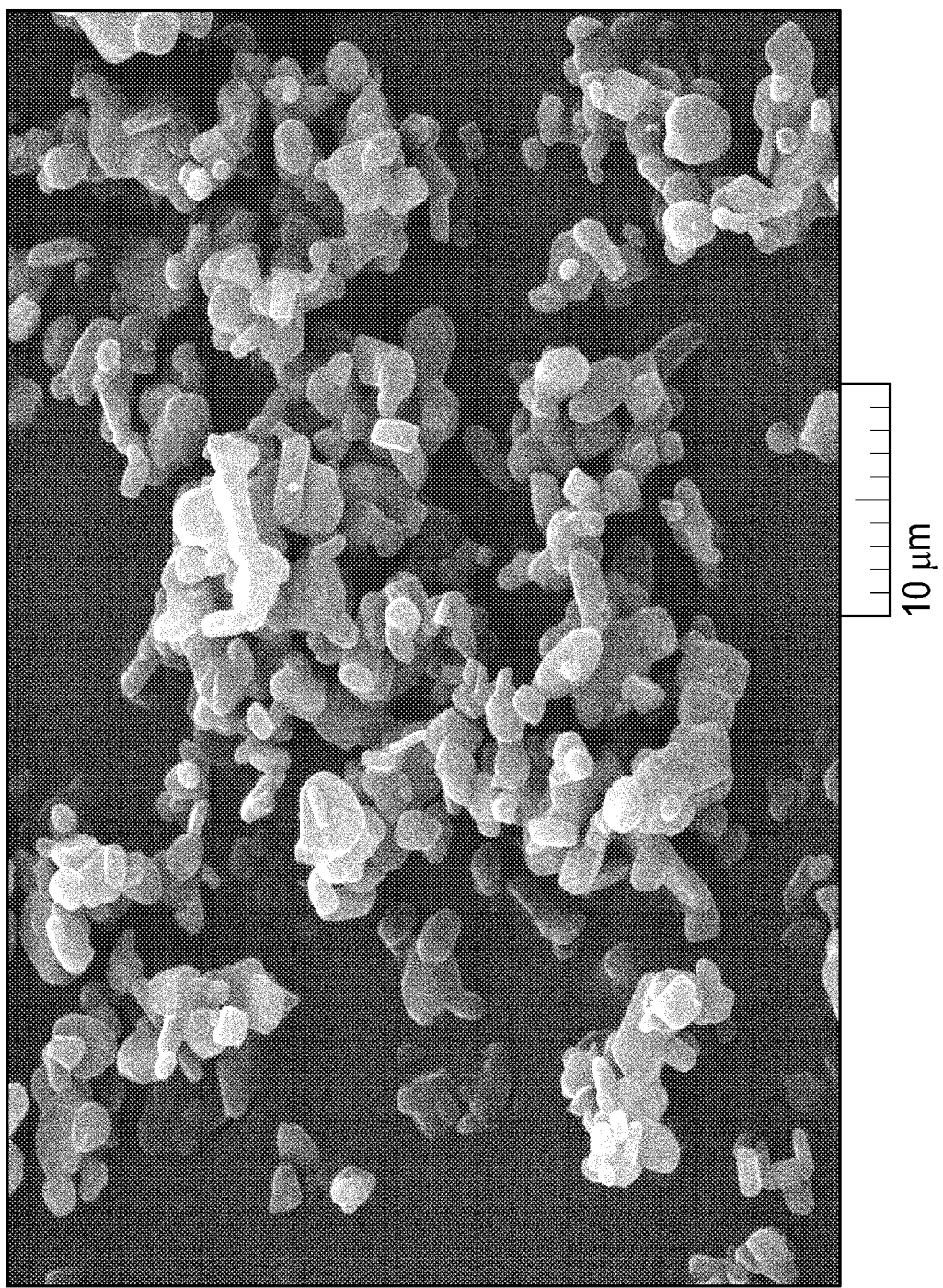
FIG. 8A illustrates an SEM image for Batch 1 after a single pass at a 10 µm scale.
Figure 8B:
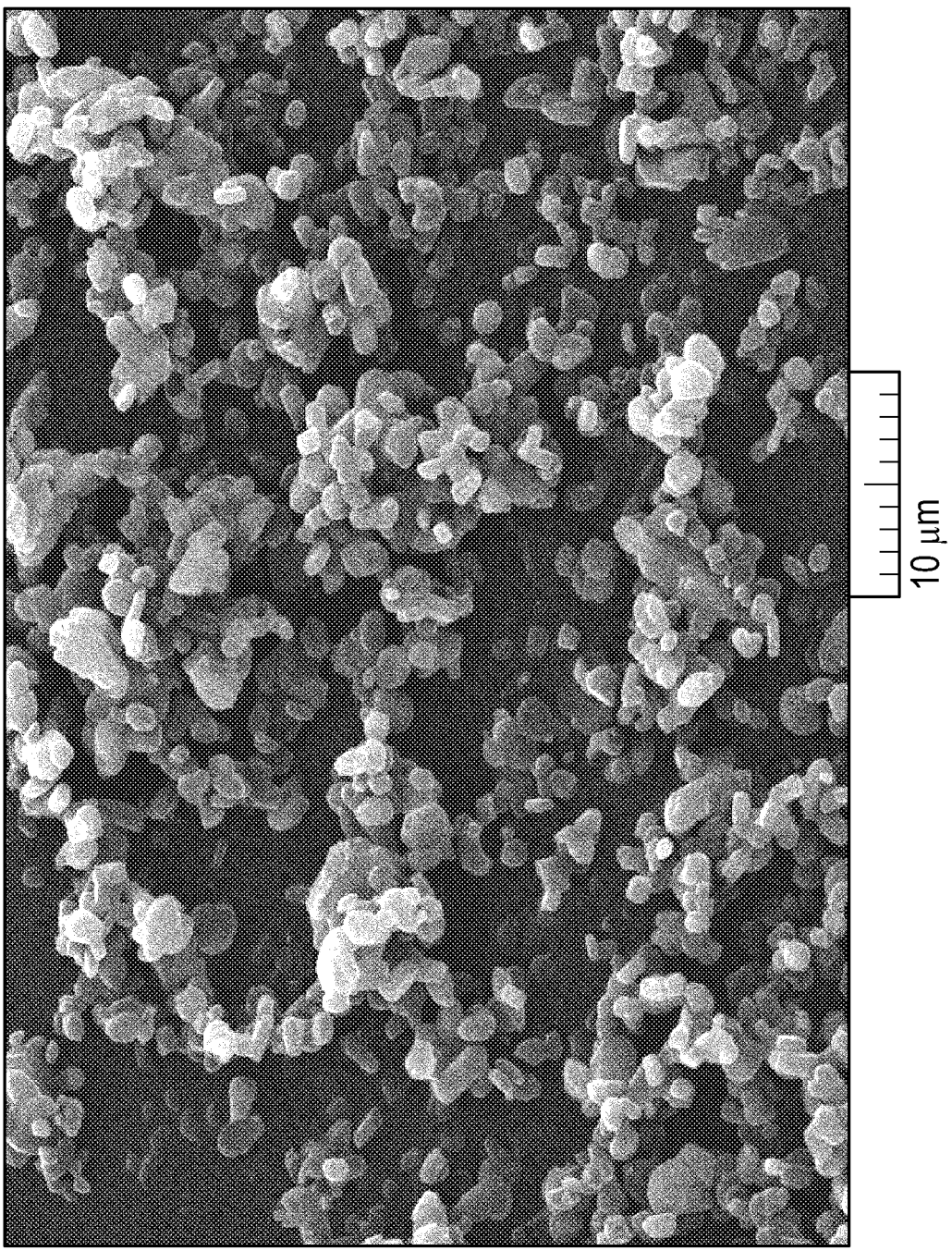
FIG. 8B illustrates an SEM image for Batch 2 after a double pass at a 10 µm scale.
Figure 9A:
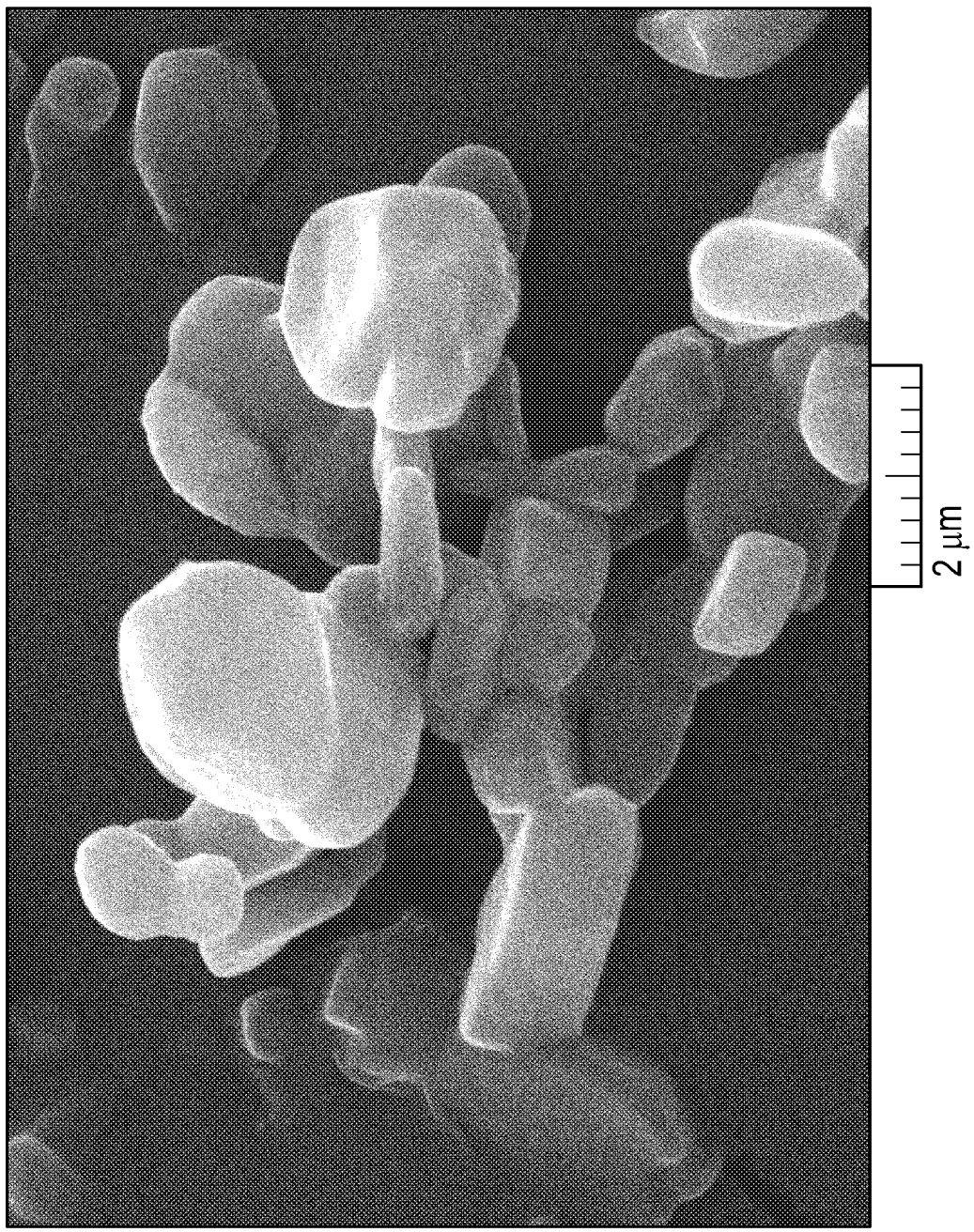
FIG. 9A illustrates an SEM image for Batch 1 after a single pass at a 2 µm scale.
Figure 9B:
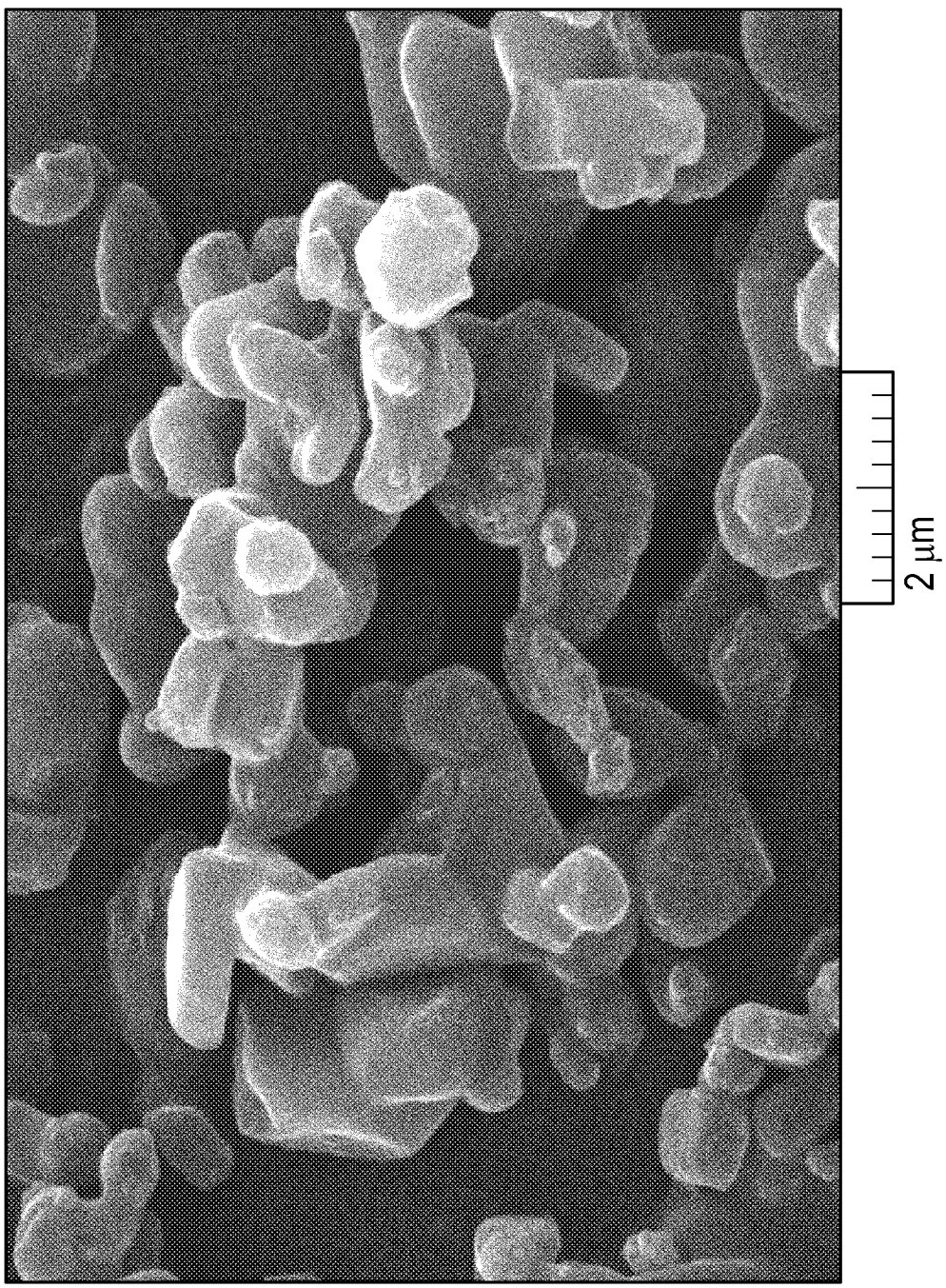
FIG. 9B illustrates an SEM image for Batch 2 after a double pass at a 2 µm scale.
Figure 10B:
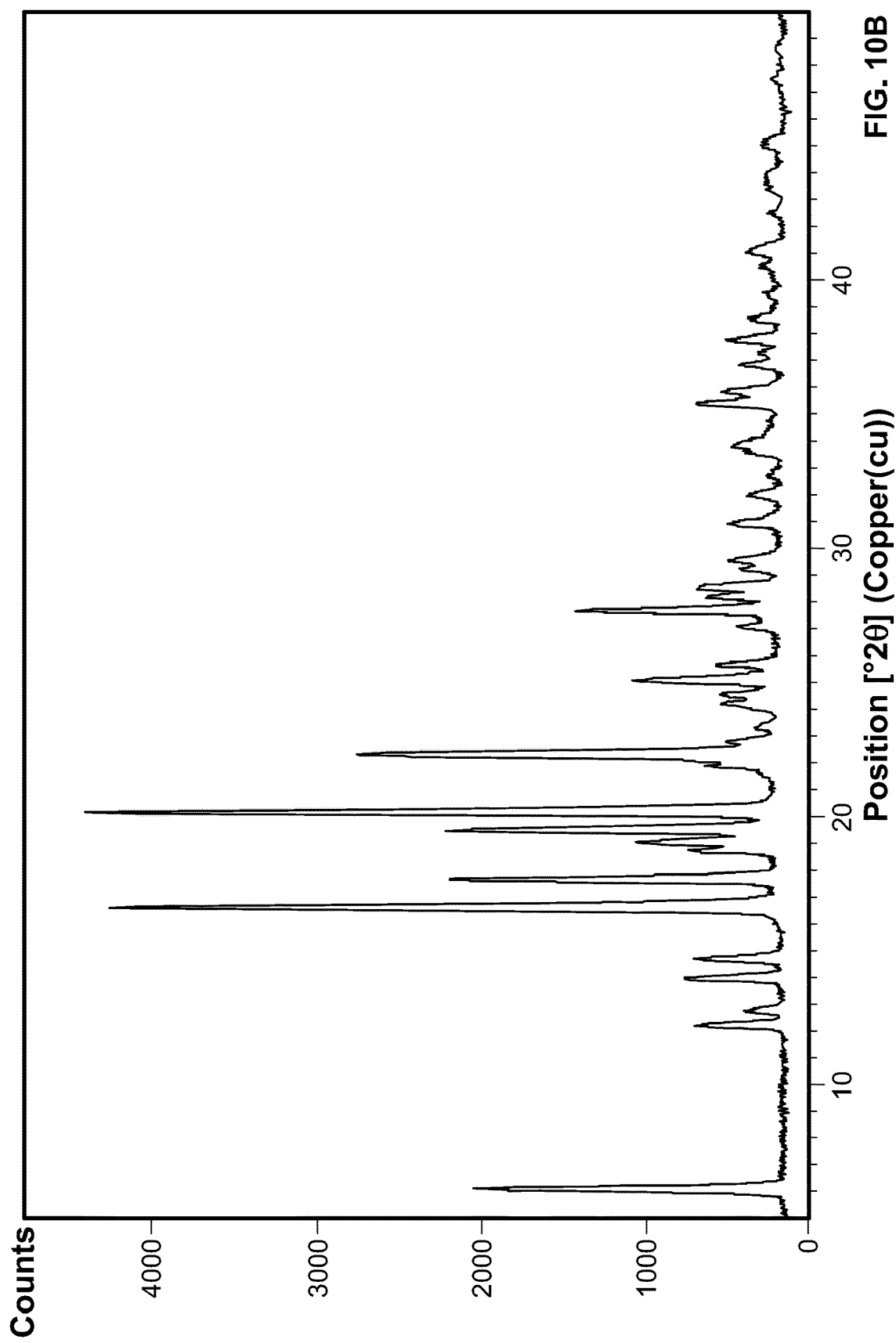
FIG. 10B illustrates a powdered x-ray diffraction pattern for Batch 2.
Figure 11A:
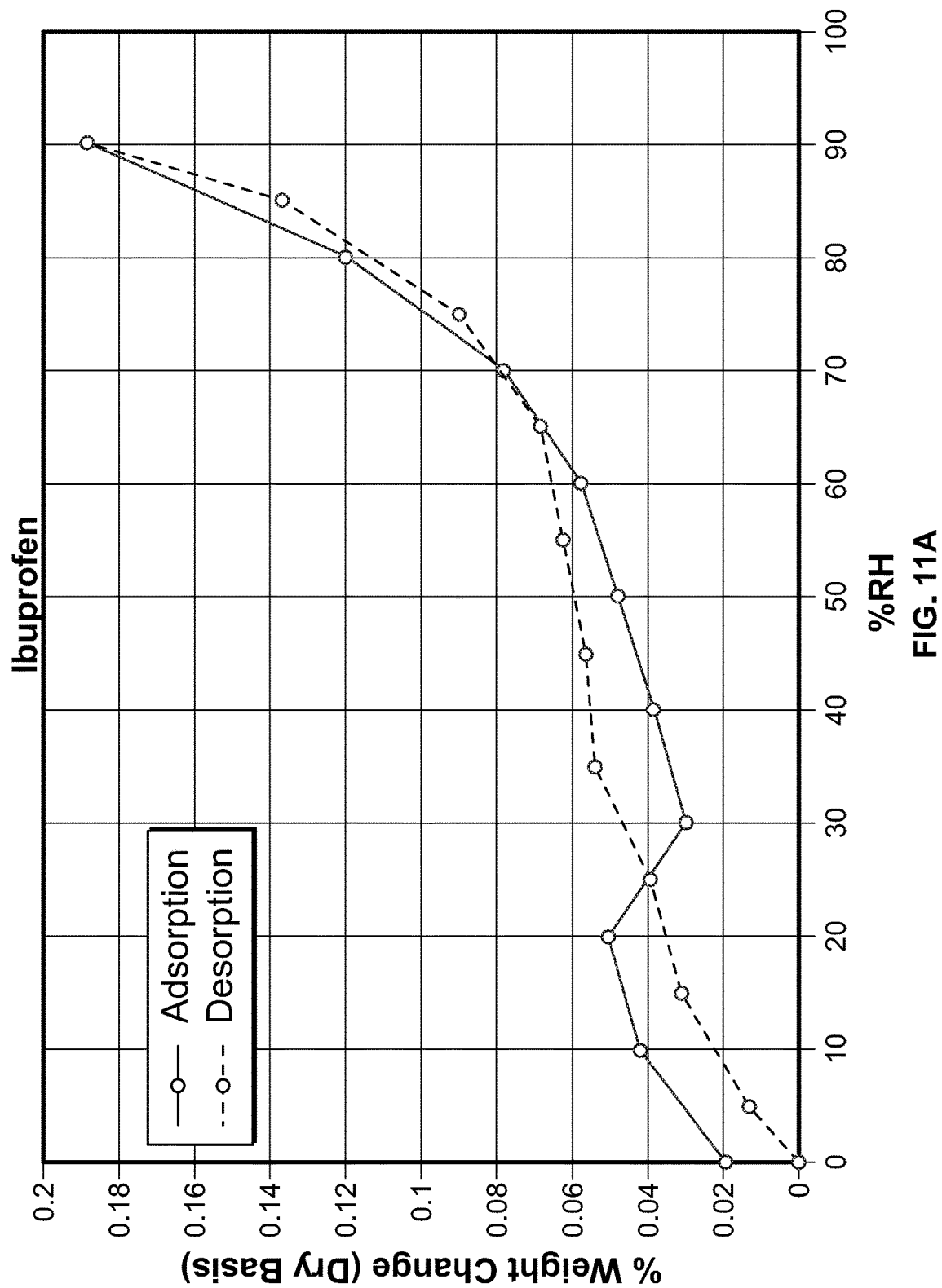
FIG. 11A illustrates a GVS pattern of coarse ibuprofen.
Figure 11B:
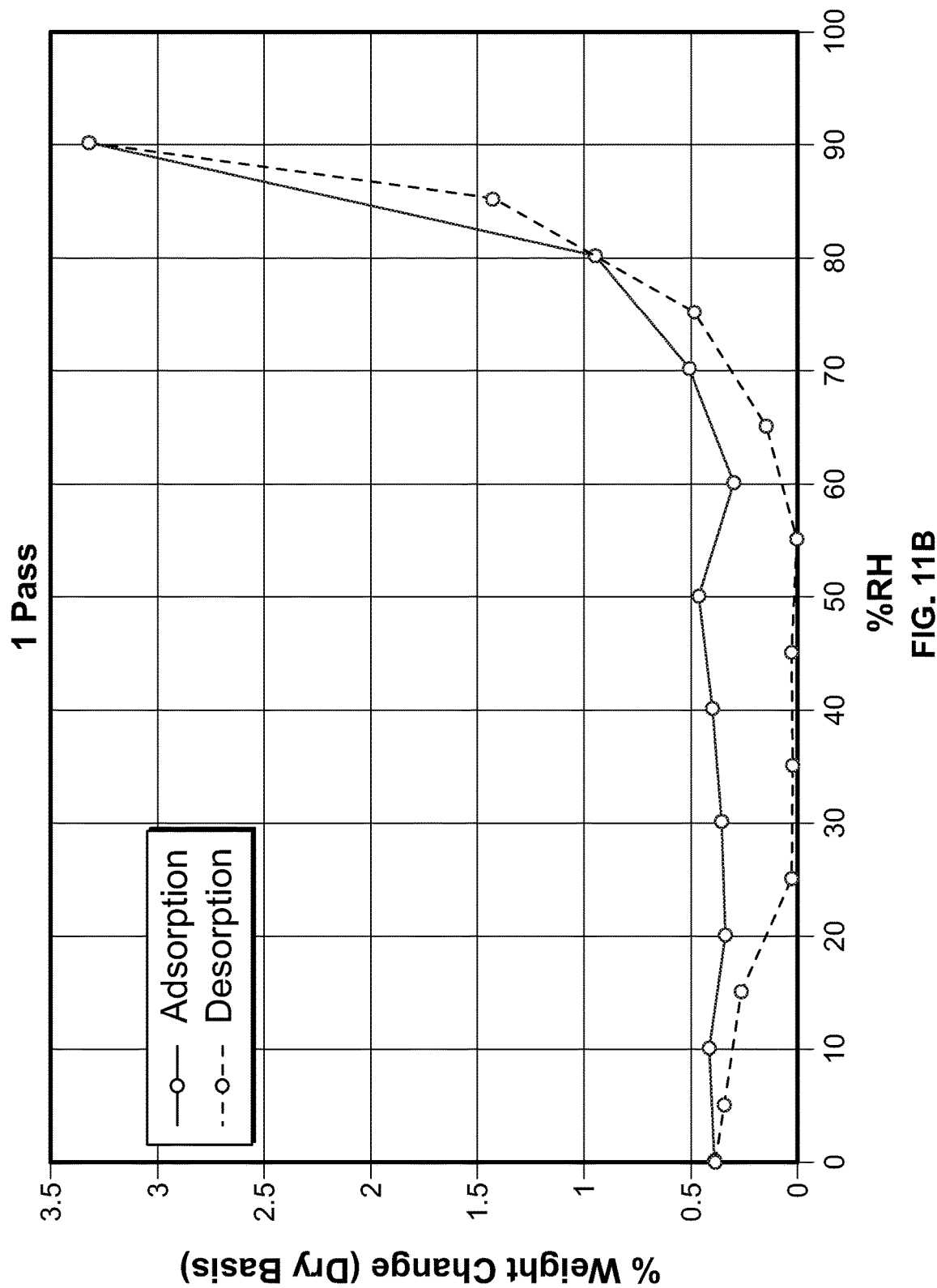
FIG. 11B illustrates a GVS pattern for Batch 1.
Figure 11C:
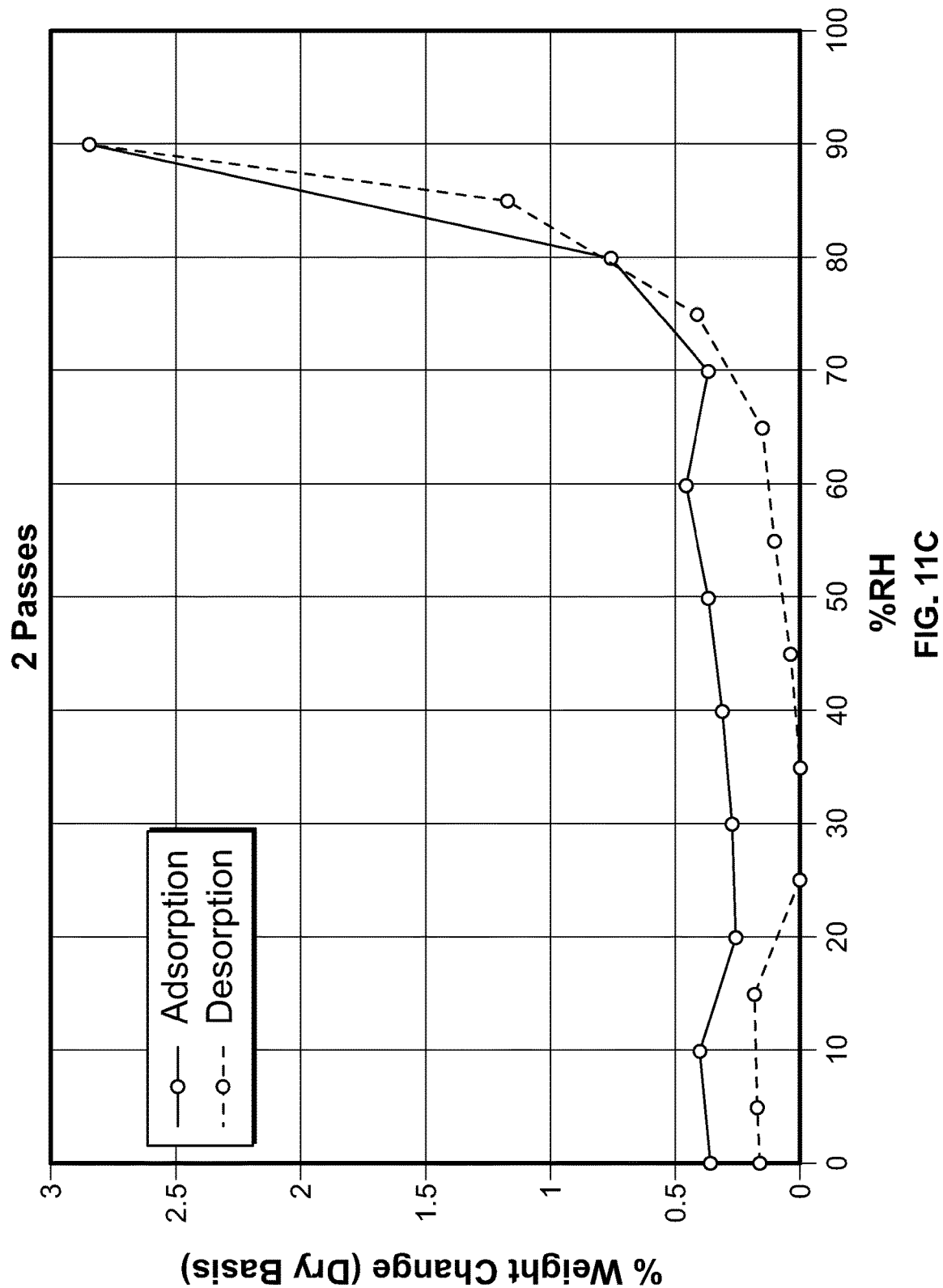
FIG. 11C illustrates a GVS pattern for Batch 2.

Following micronization, Particle Size Distribution (PSD) analysis was performed by wet dispersion. It was observed that micronized ibuprofen did not disperse well in either aqueous or organic dispersing media as micronized ibuprofen, it was highly soluble in organic solvents, was not dispersible in water and formed agglomerates, and was soluble in different surfactant containing aqueous media even at low surfactant concentrations, as observed with reducing % obscuration in the PSD analyzer instrument. Due to the limitations of PSD analysis by wet dispersion, SEM imagery was performed to infer PSD. FIGS. 8A and 8B illustrate the SEM imagery of micronized ibuprofen at a 10 μm scale for Batch 1 and Batch 2, respectively. FIGS. 9A and 9B illustrate the SEM imagery of micronized ibuprofen at a 2 μm scale for Batch 1 and Batch 2, respectively. FIGS. 10A and 10B illustrate the PXRD of micronized ibuprofen for Batch 1 and Batch 2, respectively. Table 7 contains the data for moisture content of micronized ibuprofen as determined by simultaneous thermal analyzer (STA), which tests both by DTA (Differential Temperature Analysis) and TG (Thermogravimetry). FIGS. 11A, 11B, and 11C illustrate the hygroscopicity as determined GVS for coarse ibuprofen (FIG. 11A), Batch 1 (FIG. 11B), and Batch 2 (FIG. 11C).

TABLE 7

Moisture Content of Micronized Ibuprofen by STA

| | Coarse | Batch 1 | Batch 2 |
|---|---|---|---|
| % Moisture content | 0.20 | 1.19 | 1.14 |
| Enthalpy change (J/g) | 131.0 | 120.5 | 94.4 |
| Inference | Crystalline | Partly amorphous exhibited by reducing enthalpy change | |

Figure 12:
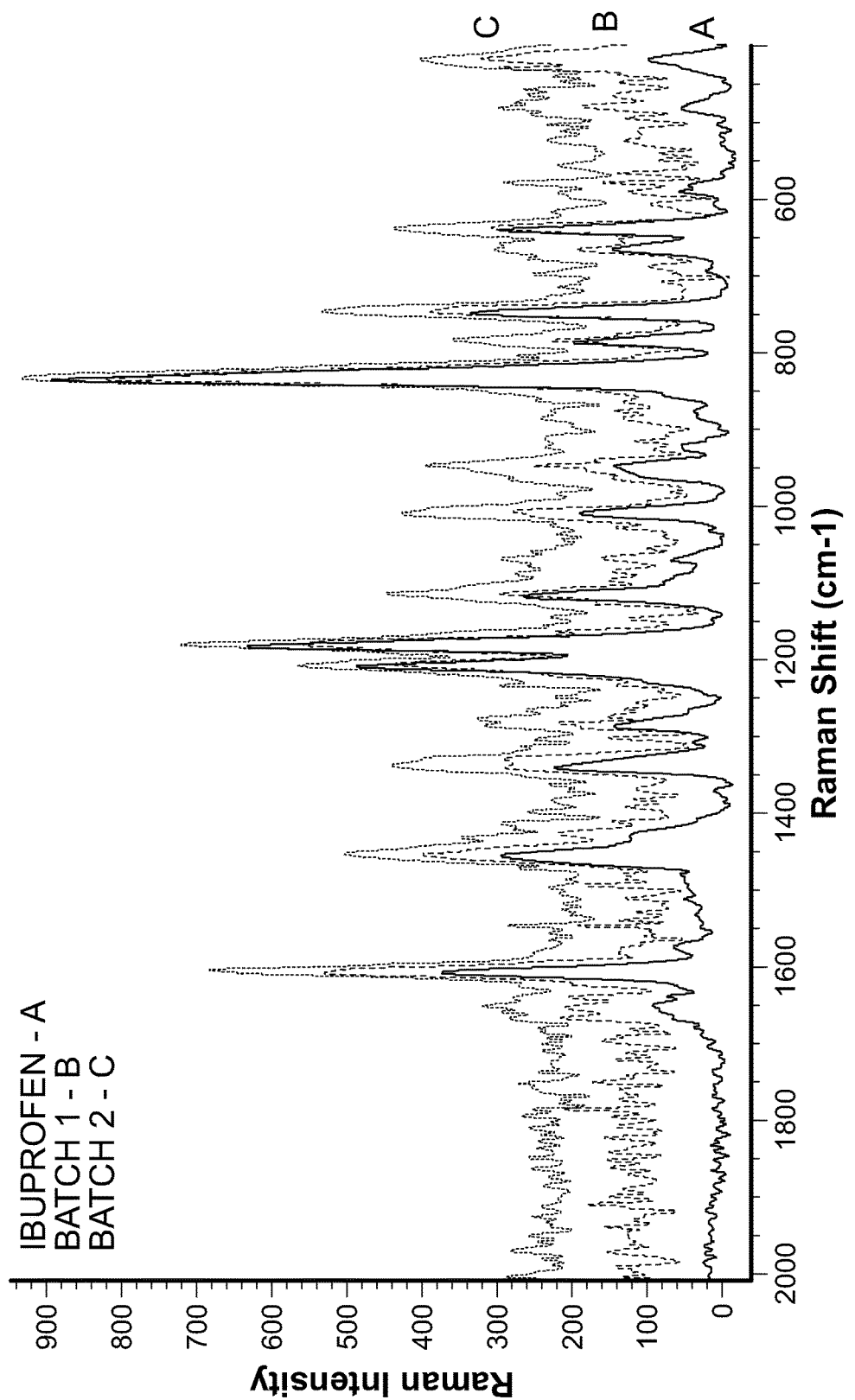
FIG. 12 illustrates a Raman spectra overlay of coarse ibuprofen, Batch 1, and Batch 2.

Micronize ibuprofen adsorbed greater moisture of ~3% on the surface compared to <0.2% adsorption on coarse ibuprofen. This increase in adsorption was due to increase surface area upon micronization and generation of surface amorphous material. FIG. 12 illustrates the Raman spectra overlay of coarse ibuprofen and micronized ibuprofen. The bottom spectra is coarse ibuprofen, followed by Batch 1, and the topmost spectra is Batch 2.

Example 4: Formulation of Cromolyn Sodium and Ibuprofen

A series of blend combinations of cromolyn sodium and coarse or micronized ibuprofen were evaluated for blend uniformity, emitted dose, and aerodynamic particulate (NGI). Ten samples were taken from geometric locations within the blend. Batch 3 consisted of cromolyn sodium and coarse ibuprofen at a weight ratio of 1.7:1 and passed through a 300 μm sieve. The blend parameters for the turbula mixer were as follows: mixing speed: 49 rpm and mix time: 10 minutes. Table 8 illustrates the results of Batch 3 that showed uniformity for cromolyn sodium and an acceptable % RSD for ibuprofen.

TABLE 8

Batch 3 Uniformity

| | % Label Claim | |
|---|---|---|
| Sample # | Cromolyn | Ibuprofen$_{course}$ |
| 1 | 102.07 | 101.29 |
| 2 | 104.94 | 99.94 |
| 3 | 102.28 | 106.17 |
| 4 | 102.57 | 105.8 |
| 5 | 100.42 | 114.83 |
| 6 | 93.05 | 124.66 |
| 7 | 103.71 | 107.54 |
| 8 | 106.23 | 102.88 |
| 9 | 107.15 | 110.57 |
| 10 | 102.34 | 101.23 |
| mean | 102.5 | 107.5 |
| % RSD | 3.8 | 7.1 |

Subsequently, the Batch 3 blend was then filled into HPMC size 3 clear capsules to a fill weight of 30 mg per capsule. The capsules were allowed to relax overnight to dissipate any static charge and then emitted dose testing was performed for five capsules. The test parameters were as follows: device: low resistance and the flowrate: 80 L/min for 3 seconds. Table 9 has the results of the emitted dose test for Batch 3.

TABLE 9

Batch 3 Emitted Dose

| Sample # | Emitted Dose (mg) | |
|---|---|---|
| | Cromolyn | Ibuprofen$_{course}$ |
| 1 | 13.487 | 5.122 |
| 2 | 13.601 | 4.594 |
| 3 | 14.186 | 5.557 |
| 4 | 12.013 | 4.116 |
| 5 | 14.258 | 5.635 |
| mean | 13.509 | 5.005 |
| % RSD | 6.7 | 12.9 |
| Observed ED from benchmark | 15 | 10 |

Batch 4 includes Batch 3 and magnesium stearate (2% w/w). Table 10 contains the results of blend uniformity testing for Batch 4. The test parameters as the same as those for Batch 3.

TABLE 10

Batch 4 Blend Uniformity

| Sample # | % Label Claim | |
|---|---|---|
| | Cromolyn | Ibuprofen$_{course}$ |
| 1 | 98.52 | 103.65 |
| 2 | 98.94 | 99.16 |
| 3 | 95.31 | 94.96 |
| 4 | 95.27 | 99.36 |
| 5 | 100.09 | 98.6 |
| 6 | 100.48 | 95.41 |
| 7 | 97.23 | 101.53 |
| 8 | 101.88 | 101.61 |
| 9 | 97.68 | 104.06 |
| 10 | 100.04 | 105.46 |
| mean | 98.5 | 100.4 |
| % RSD | 2.2 | 3.5 |

Subsequently, the Batch 4 blend was then filled into HPMC size 3 clear capsules to a fill weight of 30 mg per capsule. The capsules were allowed to relax overnight to dissipate any static charge and then emitted dose testing was performed for five capsules. The test parameters were as follows: device: low resistance and the flowrate: 80 L/min for 3 seconds. Table 11 has the results of the emitted dose test for Batch 4.

TABLE 11

Batch 4 emitted dose

| Sample # | Emitted Dose (mg) | |
|---|---|---|
| | Cromolyn | Ibuprofen$_{course}$ |
| 1 | 15.668 | 5.615 |
| 2 | 15.059 | 5.686 |
| 3 | 15.955 | 5.456 |
| 4 | 15.973 | 5.585 |
| 5 | 17.969 | 5.130 |
| mean | 16.125 | 5.495 |
| % RSD | 6.8 | 4.0 |
| Observed ED from benchmark | 15 | 10 |

The concentration of coarse ibuprofen was increased to determine the effect on emitted dose performance. Three batches were made adding magnesium stearate:Batch 5 (weight ratio cromolyn sodium:ibuprofen 1.7:1.1); Batch 6 (weight ratio cromolyn sodium:ibuprofen 1.7:1.5); and Batch 7 (weight ratio cromolyn sodium:ibuprofen 1.7:2.0). Table 12 illustrates the blend uniformity for batches 4, 5, 6, and 7. The blends were homogeneous.

TABLE 12

Blend uniformity for Batches 4, 5, 6, and 7.

| | Batch 4 | | Batch 5 | | Batch 6 | | Batch 7 | |
|---|---|---|---|---|---|---|---|---|
| Sample # | Crmlyn | Ibuprfn | Crmlyn | Ibuprfn | Crmlyn | Ibuprfn | Crmlyn | Ibuprfn |
| 1 | 98.52 | 103.65 | 104.66 | 95.01 | 99.42 | 87.21 | 111.17 | 93.72 |
| 2 | 98.94 | 99.16 | 100.29 | 100.72 | 93.10 | 98.52 | 102.58 | 83.07 |
| 3 | 95.31 | 94.96 | 96.77 | 104.56 | 97.05 | 98.46 | 105.13 | 85.56 |
| 4 | 95.27 | 99.36 | 101.94 | 97.85 | 94.35 | 96.46 | 101.07 | 86.49 |
| 5 | 100.09 | 98.6 | 99.26 | 99.19 | 93.74 | 94.66 | 96.4 | 84.65 |
| 6 | 100.48 | 95.41 | 103.43 | 98.3 | 96.33 | 99.77 | 105.64 | 83.45 |
| 7 | 97.23 | 101.53 | 99.35 | 101.56 | 94.37 | 100.2 | 104.58 | 86.6 |
| 8 | 101.88 | 101.61 | 105.96 | 97.13 | 95.09 | 96.29 | 94.88 | 79.87 |
| 9 | 97.68 | 104.06 | 98.66 | 95.81 | 93.27 | 100.86 | 103.45 | 84.96 |
| 10 | 100.04 | 105.46 | 103.76 | 97.84 | 97.62 | 98.25 | 101.35 | 85.51 |
| mean | 98.5 | 100.4 | 101.4 | 98.8 | 95.4 | 97.1 | 102.6 | 85.4 |
| % RSD | 2.2 | 3.5 | 2.9 | 2.9 | 2.2 | 4.1 | 4.5 | 4.1 |

Using the same parameters as before, the emitted dose testing results are summarized in Table 13.

TABLE 13

Emitted Dose Testing for Batched 4, 5, 6, and 7.

| | Batch 4 | | Batch 5 | | Batch 6 | | Batch 7 | |
|---|---|---|---|---|---|---|---|---|
| | Fill weight | | | | | | | |
| | 30 mg | | 32 mg | | 35 mg | | 40 mg | |
| Sample # | Crmlyn | Ibuprfn | Crmlyn | Ibuprfn | Crmlyn | Ibuprfn | Crmlyn | Ibuprfn |
| 1 | 13.487 | 5.122 | 14.49 | 10.651 | 13.536 | 16.057 | 14.29 | 18.668 |
| 2 | 13.601 | 4.594 | 13.331 | 10.451 | 14.618 | 14.417 | 14.656 | 17.882 |
| 3 | 14.186 | 5.557 | 13.851 | 10.004 | 14.006 | 15.378 | 15.564 | 18.916 |
| 4 | 12.013 | 4.116 | 13.42 | 9.635 | 15.235 | 15.161 | 14.32 | 17.093 |
| 5 | 14.258 | 5.635 | 12.922 | 10.148 | 14.478 | 15.072 | 13.417 | 19.011 |
| mean | 13.509 | 5.005 | 13.603 | 10.178 | 14.375 | 15.217 | 14.449 | 18.314 |
| % RSD | 6.7 | 12.9 | 4.4 | 3.9 | 4.5 | 3.9 | 5.4 | 4.4 |

The results show that by increasing the fill weight of Ibuprofen there was an increase in the emitted dose. Cromolyn sodium maintained consistent performance for the emitted dose regardless of the Ibuprofen concentration.

Magnesium stearate was removed from the formulation of Batch 5 to obtain Batch 8. Table 14 illustrates the blend uniformity testing for Batch 8, which was a homogeneous powder blend. Table 15 contains the data for emitted dose testing of Batch 5 and Batch 8.

TABLE 14

Blend Uniformity for Batch 8

| | Batch 8 | |
|---|---|---|
| Sample # | Cromolyn | Ibuprofen$_{course}$ |
| 1 | 84.98 | 88.33 |
| 2 | 86.67 | 87.98 |
| 3 | 87.57 | 87.69 |
| 4 | 91.89 | 90.43 |
| 5 | 94.21 | 91.35 |
| 6 | 88.82 | 92.93 |
| 7 | 90.61 | 92.7 |
| 8 | 90.64 | 90.96 |
| 9 | 89.41 | 95.35 |
| 10 | 90.92 | 92.2 |
| mean | 89.6 | 91.0 |
| % RSD | 3.0 | 2.7 |

TABLE 15

Emitted Dose comparison between Batch 5 and Batch 8

| | Batch 5 (32 mg) | | Batch 8 (32 mg) | |
|---|---|---|---|---|
| | Cromolyn | Ibuprofen | Cromolyn | Ibuprofen |
| 1 | 14.49 | 10.651 | 14.929 | 10.547 |
| 2 | 13.331 | 10.451 | 15.102 | 10.627 |
| 3 | 13.851 | 10.004 | 15.271 | 10.078 |
| 4 | 13.42 | 9.635 | 16.544 | 10.142 |
| 5 | 12.922 | 10.148 | 15.996 | 10.349 |
| mean | 13.603 | 10.178 | 15.568 | 10.349 |
| % RSD | 4.4 | 3.9 | 4.4 | 2.3 |

Example 5: Formulation of Cromolyn Sodium and Ibuprofen

Two formulations were made using a blend of micronized ibuprofen and magnesium stearate and another without magnesium stearate. Batch 9 with 2% by weight magnesium stearate and Batch 10 without magnesium stearate. The blending process comprises the steps (1) micronizing ibuprofen at a feed pressure of 45 psi and a grinding pressure of 45 psi for one pass; (2) separately passing the micronized ibuprofen and cromolyn sodium through a 300 µm sieve; (3) blending the two materials in a Turbula mixer for 10 minutes at 49 rpm; and (4) blend co-milling by milling the blend (single pass) with a feed pressure of 45 psi and grinding pressure of 45 psi. Table 14 summarizes the assay results for the two batches without magnesium stearate.

TABLE 16

Results - Assay without magnesium stearate

| | Batch 9 | | Batch 10 | |
|---|---|---|---|---|
| | Cromolyn (0.584 mg) | Ibuprofen (0.344 mg) | Cromolyn (0.596 mg) | Ibuprofen (0.351 mg) |
| 1 | 107.63 | 89.52 | 106.44 | 87.65 |
| 2 | 99.93 | 85.83 | 102.83 | 85.03 |
| mean | 103.8 | 87.7 | 104.6 | 86.3 |
| % RSD | 5.2 | 3.0 | 2.4 | 2.1 |

Table 15 summarizes the assay results for the two batches with magnesium stearate.

TABLE 17

Results - Assay with magnesium stearate

| | Batch 9 (40 mg) | | Batch 10 (40 mg) | |
|---|---|---|---|---|
| | Cromolyn | Ibuprofen | Cromolyn | Ibuprofen |
| 1 | 17.889 | 10.961 | 17.262 | 10.649 |
| 2 | 16.516 | 10.562 | 18.199 | 10.894 |
| 3 | 17.568 | 10.667 | 17.71 | 10.618 |
| 4 | 17.368 | 10.606 | 18.144 | 10.913 |
| 5 | 25.334* | 15.327* | 17.207 | 10.474 |
| mean | 17.335 | 10.699 | 17.704 | 10.71 |
| % RSD | 3.4 | 1.7 | 2.7 | 1.8 |

The results show no difference between formulation with and without magnesium stearate in terms of emitted dose. Both batches were tested for NGI and stability.

Aerodynamic particle size distribution determined by NGI. Batch 9 was co-milled and magnesium stearate was added. Batch 10 was co-milled and had no magnesium stearate. Batch 5 was blended with coarse ibuprofen and magnesium stearate was added. Batch 8 was blended with coarse ibuprofen and had no magnesium stearate. Table 18 summarizes the conditions used in the NGI method.

TABLE 18

| | |
|---|---|
| Type & Size of Capsules | Clear HPMC size 3 capsules |
| Fill weights | Batch 9 and Batch 10: 40 mg |
| | Batch 5 and Batch 8: 32 mg |
| Number of shots | 1 |
| Coating solution used | 1 mg/mL Pluronic F68 and 3% v/v PEG400 in Acetone |
| Volume of the coating solution used in each of the cups | Cups 1, MOC: 3 mL |
| | Cups 2-7: 1.5 mL |
| Diluents used | 25 mM potassium phosphate buffer pH 6.8:Methanol (1:1) |
| Device used | Low resistance device |

TABLE 18-continued

| | |
|---|---|
| Flow rate | 80 L/min for 3 seconds |
| Dilution used | Device + capsule: 50 mL |
| | Throat (induction port): 50 mL |
| | Pre-separator: 100 mL |
| | Stages 1-7, MOC: 10 mL |
| Number of Replicates per formulation | 3 |

Tables 19-22 summarize the data for each batch. Table 23 contains the data comparing batches 5, 8, 9, and 10.

TABLE 19

NGI Results of Batch 9.

| | API | | | | | | | |
|---|---|---|---|---|---|---|---|---|
| | Cromolyn | | | | Ibuprofen | | | |
| | Shots fired | | | | | | | |
| | 1 | | | | 1 | | | |
| | Batch Strength | | | | | | | |
| | 23.36 mg | | | | 13.76 mg | | | |
| | Device Number | | | | | | | |
| Stage of Use | 1 | 2 | 3 | Mean | 4 | 5 | 6 | Mean |
| Device | 3.90 | 3.93 | 3.93 | 3.9 | 2.20 | 2.19 | 2.23 | 2.2 |
| Throat | 2.22 | 2.17 | 2.22 | 2.2 | 1.02 | 1.02 | 1.01 | 1.0 |
| Pre-sep | 0.58 | 0.64 | 0.63 | 0.6 | 0.29 | 0.33 | 0.30 | 0.3 |
| Stage 1 | 0.94 | 1.08 | 0.87 | 1.0 | 0.54 | 0.63 | 0.49 | 0.6 |
| Stage 2 | 5.27 | 5.05 | 5.10 | 5.1 | 2.60 | 2.57 | 2.53 | 2.6 |
| Stage 3 | 4.77 | 4.63 | 5.01 | 4.8 | 2.49 | 2.47 | 2.61 | 2.5 |
| Stage 4 | 2.58 | 2.38 | 2.60 | 2.5 | 1.70 | 1.60 | 1.72 | 1.7 |
| Stage 5 | 0.83 | 0.75 | 0.79 | 0.8 | 0.54 | 0.50 | 0.53 | 0.5 |
| Stage 6 | 0.29 | 0.27 | 0.28 | 0.3 | 0.16 | 0.15 | 0.16 | 0.2 |
| Stage 7 | 0.09 | 0.08 | 0.08 | 0.1 | 0.05 | 0.04 | 0.04 | 0.0 |
| MOC | 0.02 | 0.02 | 0.02 | 0.0 | 0.01 | 0.01 | 0.01 | 0.0 |
| Total recovery | 21.50 | 21.00 | 21.53 | 21.3 | 11.60 | 11.51 | 11.64 | 11.6 |
| Total ex-device | 17.60 | 17.07 | 17.61 | 17.4 | 9.40 | 9.32 | 9.41 | 9.4 |
| FPM | 8.59 | 8.13 | 8.79 | 8.5 | 4.95 | 4.77 | 5.08 | 4.9 |
| FPF | 48.79 | 47.64 | 49.93 | 48.8 | 52.65 | 51.19 | 53.93 | 52.6 |
| % Recovery | 92.04 | 89.88 | 92.18 | 91.4 | 84.27 | 83.66 | 84.61 | 84.2 |

TABLE 20

NGI Results of Batch 10

| | API | | | | | | |
|---|---|---|---|---|---|---|---|
| | Cromolyn | | | | Ibuprofen | | |
| | Shots fired | | | | | | |
| | 1 | | | | 1 | | |
| | Batch Strength | | | | | | |
| | 23.84 mg | | | | 14.04 mg | | |
| | Device Number | | | | | | |
| Stage of Use | 1 | 2 | 3 | Mean | 4 | 5 | 6 |
| Device | 3.49 | 3.88 | 4.42 | 3.9 | 1.87 | 2.09 | 2.55 |
| Throat | 1.73 | 2.32 | 2.06 | 2.0 | 0.90 | 1.08 | 1.00 |
| Pre-sep | 0.50 | 0.64 | 0.73 | 0.6 | 0.26 | 0.32 | 0.38 | 0.3 |
| Stage 1 | 0.90 | 1.01 | 1.37 | 1.1 | 0.51 | 0.59 | 0.82 | 0.6 |
| Stage 2 | 5.69 | 5.82 | 5.75 | 5.8 | 2.80 | 2.91 | 2.87 | 2.9 |
| Stage 3 | 5.49 | 4.92 | 4.33 | 4.9 | 2.79 | 2.59 | 2.33 | 2.6 |
| Stage 4 | 2.72 | 2.38 | 2.32 | 2.5 | 1.75 | 1.57 | 1.51 | 1.6 |

TABLE 20-continued

NGI Results of Batch 10

| | API | | | | | | |
|---|---|---|---|---|---|---|---|
| | Cromolyn | | | | Ibuprofen | | |
| | Shots fired | | | | | | |
| | 1 | | | | 1 | | |
| | Batch Strength | | | | | | |
| | 23.84 mg | | | | 14.04 mg | | |
| | Device Number | | | | | | |
| Stage of Use | 1 | 2 | 3 | Mean | 4 | 5 | 6 |
| Stage 5 | 0.78 | 0.71 | 0.65 | 0.7 | 0.49 | 0.44 | 0.39 | 0.4 |
| Stage 6 | 0.27 | 0.25 | 0.24 | 0.3 | 0.12 | 0.11 | 0.10 | 0.1 |
| Stage 7 | 0.07 | 0.06 | 0.07 | 0.1 | 0.03 | 0.03 | 0.03 | 0.0 |
| MOC | 0.00 | 0.00 | 0.00 | 0.0 | 0.01 | 0.01 | 0.01 | 0.0 |
| Total recovery | 21.64 | 21.98 | 21.94 | 21.9 | 11.53 | 11.71 | 11.97 | 11.7 |
| Total ex-device | 18.15 | 18.10 | 17.52 | 17.9 | 9.66 | 9.63 | 9.42 | 9.6 |
| FPM | 9.33 | 8.32 | 7.61 | 8.4 | 5.19 | 4.73 | 4.35 | 4.8 |
| FPF | 51.39 | 45.95 | 43.43 | 46.9 | 53.71 | 49.12 | 46.23 | 49.7 |
| % Recovery | 90.77 | 92.19 | 92.01 | 91.7 | 82.09 | 83.43 | 85.23 | 83.6 |

TABLE 21

NGI Results of Batch 5.

| | API | | | | | | | |
|---|---|---|---|---|---|---|---|---|
| | Cromolyn | | | | Ibuprofen | | | |
| | Shots fired | | | | | | | |
| | 1 | | | | 1 | | | |
| | Batch Strength | | | | | | | |
| | 18.048 mg | | | | 11.68 mg | | | |
| | Device Number | | | | | | | |
| Stage of Use | 1 | 2 | 3 | Mean | 4 | 5 | 6 | Mean |
| Device | 2.02 | 2.03 | 2.06 | 2.0 | 0.52 | 0.52 | 0.38 | 0.5 |
| Throat | 3.33 | 3.32 | 3.93 | 3.5 | 1.30 | 1.30 | 1.00 | 1.2 |
| Pre-sep | 2.31 | 2.07 | 2.08 | 2.2 | 7.93 | 6.56 | 6.40 | 7.0 |
| Stage 1 | 0.51 | 0.60 | 0.63 | 0.6 | 0.88 | 1.53 | 1.59 | 1.3 |
| Stage 2 | 1.69 | 1.74 | 1.77 | 1.7 | 0.18 | 0.17 | 0.17 | 0.2 |
| Stage 3 | 2.37 | 2.25 | 2.30 | 2.3 | 0.08 | 0.06 | 0.06 | 0.1 |
| Stage 4 | 2.22 | 1.94 | 1.99 | 2.1 | 0.05 | 0.04 | 0.04 | 0.0 |
| Stage 5 | 1.37 | 1.19 | 1.22 | 1.3 | 0.02 | 0.02 | 0.02 | 0.0 |
| Stage 6 | 0.62 | 0.56 | 0.58 | 0.6 | 0.01 | 0.01 | 0.01 | 0.0 |
| Stage 7 | 0.21 | 0.20 | 0.20 | 0.2 | 0.00 | 0.00 | 0.00 | 0.0 |
| MOC | 0.10 | 0.07 | 0.08 | 0.1 | 0.00 | 0.00 | 0.00 | 0.0 |
| Total recovery | 16.76 | 15.97 | 16.83 | 16.5 | 10.98 | 10.21 | 9.67 | 10.3 |
| Total ex-device | 14.73 | 13.94 | 14.77 | 14.5 | 10.46 | 9.69 | 9.29 | 9.8 |
| FPM | 6.89 | 6.22 | 6.37 | 6.5 | 0.17 | 0.13 | 0.13 | 0.1 |
| FPF | 46.77 | 44.58 | 43.12 | 44.8 | 1.58 | 1.30 | 1.38 | 1.4 |
| % Recovery | 92.84 | 88.46 | 93.27 | 91.5 | 94.03 | 87.41 | 82.78 | 88.1 |

TABLE 22

NGI Results of Batch 8.

| | API | | | | | | | |
|---|---|---|---|---|---|---|---|---|
| | Cromolyn | | | | Ibuprofen | | | |
| | Shots fired | | | | | | | |
| | 1 | | | | 1 | | | |
| | Batch Strength | | | | | | | |
| | 18.432 mg | | | | 11.936 mg | | | |
| | Device Number | | | | | | | |
| Stage of Use | 1 | 2 | 3 | Mean | 4 | 5 | 6 | Mean |
| Device | 1.82 | 2.13 | 2.21 | 2.1 | 0.30 | 0.43 | 0.62 | 0.4 |
| Throat | 2.88 | 3.09 | 3.14 | 3.0 | 2.05 | 2.04 | 1.67 | 1.9 |
| Pre-sep | 2.45 | 2.57 | 2.57 | 2.5 | 7.89 | 7.65 | 7.65 | 7.7 |
| Stage 1 | 0.53 | 0.54 | 0.54 | 0.5 | 0.79 | 0.70 | 0.71 | 0.7 |
| Stage 2 | 1.39 | 1.32 | 1.25 | 1.3 | 0.13 | 0.16 | 0.19 | 0.2 |
| Stage 3 | 2.55 | 2.38 | 2.31 | 2.4 | 0.05 | 0.05 | 0.06 | 0.1 |
| Stage 4 | 3.10 | 2.81 | 2.80 | 2.9 | 0.04 | 0.03 | 0.04 | 0.0 |
| Stage 5 | 1.75 | 1.66 | 1.78 | 1.7 | 0.02 | 0.02 | 0.02 | 0.0 |
| Stage 6 | 0.55 | 0.60 | 0.76 | 0.6 | 0.01 | 0.01 | 0.01 | 0.0 |
| Stage 7 | 0.11 | 0.16 | 0.26 | 0.2 | 0.00 | 0.00 | 0.00 | 0.0 |
| MOC | 0.05 | 0.05 | 0.09 | 0.1 | 0.00 | 0.00 | 0.00 | 0.0 |
| Total recovery | 17.18 | 17.30 | 17.72 | 17.4 | 11.26 | 11.08 | 10.97 | 11.1 |
| Total ex-device | 15.36 | 15.16 | 15.51 | 15.3 | 10.96 | 10.65 | 10.36 | 10.7 |
| FPM | 8.11 | 7.65 | 8.01 | 7.9 | 0.11 | 0.11 | 0.14 | 0.1 |
| FPF | 52.82 | 50.47 | 51.62 | 51.6 | 1.02 | 1.01 | 1.34 | 1.1 |
| % Recovery | 93.19 | 93.84 | 96.11 | 94.4 | 94.35 | 92.82 | 91.94 | 93.0 |

TABLE 23

Data Comparison between Batches 5, 8, 9, and 10.

| | Formulation | | | | | | | | | |
|---|---|---|---|---|---|---|---|---|---|---|
| | Co-milled | | | | Blended—coarse Ibuprofen | | | | Feasibility Batch* | |
| | Formulation Code | | | | | | | | | |
| | Batch 9 | | Batch 10 | | Batch 5 | | Batch 8 | | 13PM792-PG67 Find batch XAX | |
| | Units | | | | | | | | | |
| | mg | % | mg | % | mg | % | mg | % | mg | % |
| Device | 3.9 | 18.3 | 3.9 | 17.8 | 2.0 | 12.0 | 2.1 | 12.1 | 1.6 | 9.6 |
| Throat | 2.2 | 10.3 | 2.0 | 9.1 | 3.5 | 21.1 | 3.0 | 17.3 | 2.1 | 12.1 |
| Pre-sep | 0.6 | 2.8 | 0.6 | 2.7 | 2.2 | 13.3 | 2.5 | 14.5 | 1.1 | 6.5 |
| Stage 1 | 1.0 | 4.7 | 1.1 | 5.0 | 0.6 | 3.6 | 0.5 | 2.9 | 0.8 | 4.6 |
| Stage 2 | 5.1 | 23.9 | 5.8 | 26.5 | 1.7 | 10.2 | 1.3 | 7.5 | 3.6 | 21.1 |
| Stage 3 | 4.8 | 22.5 | 4.9 | 22.4 | 2.3 | 13.9 | 2.4 | 13.9 | 3.3 | 19.4 |
| Stage 4 | 2.5 | 11.7 | 2.5 | 11.4 | 2.1 | 12.7 | 2.9 | 16.8 | 2.6 | 15.4 |
| Stage 5 | 0.8 | 3.8 | 0.7 | 3.2 | 1.3 | 7.8 | 1.7 | 9.8 | 1.3 | 7.8 |
| Stage 6 | 0.3 | 1.4 | 0.3 | 1.4 | 0.6 | 3.6 | 0.6 | 3.5 | 0.4 | 2.4 |
| Stage 7 | 0.1 | 0.5 | 0.1 | 0.5 | 0.2 | 1.2 | 0.2 | 1.2 | 0.1 | 0.6 |
| MOC | 0.0 | 0.0 | 0.0 | 0.0 | 0.1 | 0.6 | 0.1 | 0.6 | 0.1 | 0.3 |
| Total Recovery | 21.3 | 100.0 | 21.9 | 100.0 | 16.6 | 100.0 | 17.3 | 100.0 | 17.0 | 100.0 |
| Total ex-device | 17.4 | 81.7 | 17.9 | 82.2 | 14.5 | 88.0 | 15.3 | 87.9 | 15.3 | 90.4 |
| FPM | 8.5 | 39.9 | 8.5 | 38.8 | 6.6 | 39.8 | 7.9 | 45.7 | 7.8 | 46.0 |
| Stage 3—MOC | 8.5 | 39.9 | 8.5 | 38.8 | 6.6 | 39.8 | 7.9 | 45.7 | 7.8 | 46.0 |
| % Recovery | 91.4 | 100.0 | 91.7 | 100.0 | 91.5 | 100.0 | 94.4 | 100.0 | 99.2 | 100.0 |

In a composition for systemic delivery rather than local delivery, deposition in Stages 3-MOC is of importance. The data demonstrated that blended formulations are superior in terms of Stages 3-MOC deposition compared to cromolyn only formulation. Batch 5 was comparable to the current formulation used in the current clinic while Batch 8 was better than the current product in terms of Stages 3-MOC. The blended formulation has shown an increase in cromolyn reaching the deep lung thereby increasing the amount of bioavailability of cromolyn into the plasma, the ibuprofen emitted dose and NGI test results both in course and micronized form show that it can reach the lung as well.

A stability study was performed to determine the compatibility of the combined APIs under accelerated degradation conditions. Separate control samples of micronized cromolyn sodium (Sample A) and micronized ibuprofen (Sample B) were included in the study to be used as a comparator to the blend of Cromolyn/Ibuprofen (Sample C). The study was performed at 40° C. and 75% relative humidity. Measurements were taken at time 0, 1 month, 2 months, and 3 months.

Tables 24A, 24B, and 24C summarize the study results for Sample A, Sample B, and Sample C, respectively.

TABLE 24A related substances in Sample A, cromolyn sodium

| | Related Substances | |
|---|---|---|
| | Individual Related Substances ≥ 0.5% | Total Impurities (%) |
| Initial T = 0 | 0.11 | 0.1 |
| 1 month | 0.11 | 0.1 |
| 2 months | 0.11 | 0.1 |
| 3 months | 0.11 | 0.1 |

TABLE 24B related substances in Sample B, micronized ibuprofen

| | Individual Related Substances ≥ 0.5% | | Total Impurities |
|---|---|---|---|
| | RRT 0.93 | RRT 1.11 | (%) |
| Initial T = 0 | 0.07 | ND | 0.1 |
| 1 month | 0.07 | 0.05 | 0.1 |
| 2 months | 0.07 | <LOQ | 0.1 |
| 3 months | 0.07 | <LOQ | 0.1 |

TABLE 24C related substances in Sample C, cromolyn sodium and ibuprofen

| | Ibuprofen | | Cromolyn sodium | |
|---|---|---|---|---|
| | Individual Related Substances ≥ 0.5% RRT 0.93 | Total Impurities (%) | Individual Related Substances ≥ 0.5% RRT 1.88 | Total Impurities (%) |
| Initial T = 0 | 0.07 | 0.1 | 0.11 | 0.1 |
| 1 month | 0.07 | 0.1 | 0.11 | 0.1 |
| 2 months | 0.07 | 0.1 | 0.11 | 0.1 |
| 3 months | 0.07 | 0.1 | 0.11 | 0.1 |

The combination of cromolyn sodium and ibuprofen had no effect on the stability of the material, and therefore the APIs were compatible in the combine formulation.

The study demonstrated that the method developed for the assay of the combined cromolyn sodium and ibuprofen composition distinguished between the two APIs without interference. The formulations using either micronized ibuprofen or coarse ibuprofen provided sufficient performance of an inhaled substance to achieve a therapeutic effect. The combined formulation enhanced the performance of cromolyn sodium by comparison to the original formulation. In other words, cromolyn concentration in the deeper regions of the lung were higher than seen with a formulation of cromolyn only with lactose.

What is claimed is:

1. A composition suitable for inhalation comprising cromolyn sodium and ibuprofen, wherein the cromolyn sodium is micronized; the cromolyn sodium and ibuprofen are present in a weight ratio of 1:1-2; and the ibuprofen has been passed through a sieve of about 200 to 600 μm.

2. The composition according to claim 1, wherein the ibuprofen is micronized.

3. The composition according to claim 1, wherein the ibuprofen has a particle size of about 250 to 500 μm.

4. The composition according to claim 1, wherein the ibuprofen has a particle size of about 300 to 400 μm.

5. The composition according to claim 1, wherein the cromolyn sodium and ibuprofen are in powdered form.

6. A method of making a composition according to claim 1, comprising micronizing cromolyn sodium, thereby forming micronized cromolyn sodium; separately sieving micronized cromolyn sodium and ibuprofen, thereby forming sieved cromolyn sodium and sieved ibuprofen; blending sieved cromolyn sodium and sieved ibuprofen, thereby forming blended cromolyn sodium and ibuprofen; and blend co-milling the blended cromolyn sodium and ibuprofen, thereby forming a composition of claim 1.

7. The method according to claim 6, wherein the sieve is a 300 to 400 μm sieve.

8. The method according to claim 6, wherein the micronizing is performed with an air jet mill.

9. The method according to claim 8, wherein the air jet mill has a feed gas pressure of about 45 psi and a grinding pressure of about 45 psi.

10. A method of treating Alzheimer's disease comprising administering a powdered composition according to claim 1.

11. The method according to claim 10, wherein the sieve is a 300 to 400 μm sieve.

12. The method according to claim 10, wherein the ibuprofen has a particle size of about ≤3 μm.

* * * * *